US010782223B2

(12) United States Patent
Koser

(10) Patent No.: US 10,782,223 B2
(45) Date of Patent: *Sep. 22, 2020

(54) LABEL-FREE CELLULAR MANIPULATION AND SORTING VIA BIOCOMPATIBLE FERROFLUIDS

(71) Applicant: Yale University, New Haven, CT (US)

(72) Inventor: Hur Koser, Branford, CT (US)

(73) Assignee: YALE UNIVERSITY, New Haven, CT (US)

(*) Notice: Subject to any disclaimer, the term of this patent is extended or adjusted under 35 U.S.C. 154(b) by 301 days.

This patent is subject to a terminal disclaimer.

(21) Appl. No.: 15/670,264

(22) Filed: Aug. 7, 2017

(65) Prior Publication Data

US 2018/0128729 A1 May 10, 2018

Related U.S. Application Data

(63) Continuation of application No. 15/163,890, filed on May 25, 2016, now Pat. No. 9,726,592, which is a (Continued)

(51) Int. Cl.
*G01N 15/10* (2006.01)
*B03C 1/32* (2006.01)
(Continued)

(52) U.S. Cl.
CPC ...... *G01N 15/1056* (2013.01); *B01L 3/50273* (2013.01); *B01L 3/502715* (2013.01);
(Continued)

(58) Field of Classification Search
CPC ....... G01N 15/1056; G01N 2015/1081; G01N 2015/0065; G01N 2015/1006;
(Continued)

(56) References Cited

U.S. PATENT DOCUMENTS 3,764,540 A 10/1973 Khalafalla et al.
5,194,133 A 3/1993 Clark et al.
(Continued)

FOREIGN PATENT DOCUMENTS

CN 101087655 12/2007
WO 2006004558 A1 1/2006

OTHER PUBLICATIONS

Kose, et al., "Towards Ferro-microfluidics for Effective and Rapid Cellular manipulation and Sorting," Proceedings of the 3rd IEEE Int. Conf. on Nano/Micro Engineered and Molecular Systems, Jan. 6-9, 2008, China, pp. 903-906, entire document, especially p. 903, col. 2, para 6, p. 904, col. 2. Para 1; p. 905, col. 1, para 1; p. 906, col. 2, para 1: Fig. 3; Fig. 4a; Fig.
(Continued)

*Primary Examiner* — Jill A Warden
*Assistant Examiner* — Brittany I Fisher
(74) *Attorney, Agent, or Firm* — Riverside Law LLP

(57) ABSTRACT

A device for separating a sample of cells suspended in a bio-compatible ferrofluid is described. The device includes a microfluidic channel having a sample inlet, at least one output, and a length between the sample inlet and the at least one output, wherein a sample can be added to the sample inlet and flow along the length to the at least one outlet. The device includes a plurality of electrodes, wherein the microfluidic channel length transverses the plurality of electrodes, and further includes a power source for applying a current to the plurality of electrodes to create a magnetic field pattern along the length of the microfluidic channel. The present invention also includes a method for separating at least one cell type. The method includes the steps of suspending cells in a bio-compatible ferrofluid to form a sample, passing the sample through a microfluidic channel that transverses a plurality of electrodes, applying a current to the plurality of
(Continued)

electrodes to create a magnetic field pattern along the length of the microfluidic channel, and sorting the cells into at least one output channel based on a variation of at least one of cell size, shape and elasticity.

37 Claims, 10 Drawing Sheets

Related U.S. Application Data continuation of application No. 14/591,492, filed on Jan. 7, 2015, now Pat. No. 9,352,317, which is a continuation of application No. 13/514,331, filed as application No. PCT/US2010/059270 on Dec. 7, 2010, now Pat. No. 8,961,878.

(60) Provisional application No. 61/267,163, filed on Dec. 7, 2009, provisional application No. 61/407,738, filed on Oct. 28, 2010.

(51) Int. Cl.
| | |
|---|---|
| B03C 1/023 | (2006.01) |
| B03C 1/23 | (2006.01) |
| B03C 1/28 | (2006.01) |
| B03C 1/253 | (2006.01) |
| B01L 3/00 | (2006.01) |
| C12M 1/00 | (2006.01) |
| C12N 13/00 | (2006.01) |
| G01N 15/00 | (2006.01) |

(52) U.S. Cl.
CPC ........ *B01L 3/502761* (2013.01); *B03C 1/023* (2013.01); *B03C 1/23* (2013.01); *B03C 1/253* (2013.01); *B03C 1/288* (2013.01); *B03C 1/32* (2013.01); *C12M 47/04* (2013.01); *C12N 13/00* (2013.01); *B01L 2200/0636* (2013.01); *B01L 2200/0652* (2013.01); *B01L 2300/06* (2013.01); *B01L 2300/0848* (2013.01); *B03C 2201/18* (2013.01); *B03C 2201/24* (2013.01); *B03C 2201/26* (2013.01); *G01N 2015/0065* (2013.01); *G01N 2015/1006* (2013.01); *G01N 2015/1081* (2013.01)

(58) Field of Classification Search
CPC ........... B03C 1/288; B03C 1/023; B03C 1/32; B03C 1/23; B03C 1/253; B03C 2201/24; B03C 2201/26; B01L 3/502761; B01L 3/50273; B01L 3/502715; B01L 2300/06; B01L 2300/0848; B01L 2200/0652; B01L 2200/0636

See application file for complete search history.

(56) References Cited

U.S. PATENT DOCUMENTS

| | | | |
|---|---|---|---|
| 5,795,470 A * | 8/1998 | Wang | A23L 3/32 210/222 |
| 6,663,757 B1 | 12/2003 | Fuhr et al. | |
| 8,961,878 B2 * | 2/2015 | Koser | B03C 1/253 422/73 |
| 9,352,317 B2 * | 5/2016 | Koser | B03C 1/253 |
| 9,726,592 B2 * | 8/2017 | Koser | B03C 1/253 |
| 2003/0159999 A1 | 8/2003 | Oakey et al. | |
| 2003/0235504 A1 | 12/2003 | Lemoff et al. | |
| 2004/0018611 A1 | 1/2004 | Ward et al. | |
| 2004/0096977 A1 * | 5/2004 | Rakestraw | G01N 15/1459 436/63 |
| 2006/0166357 A1 * | 7/2006 | Takayama | B01L 3/50273 435/289.1 |
| 2007/0037225 A1 * | 2/2007 | Metzger | G01N 33/5438 435/7.22 |
| 2007/0125941 A1 | 6/2007 | Lee et al. | |
| 2007/0134809 A1 | 6/2007 | Cho et al. | |
| 2007/0196820 A1 | 8/2007 | Kapur et al. | |
| 2007/0215553 A1 | 9/2007 | Yellen et al. | |
| 2008/0148821 A1 * | 6/2008 | Donsky | G01N 13/04 73/64.47 |
| 2008/0255006 A1 | 10/2008 | Wang et al. | |
| 2008/0302732 A1 | 12/2008 | Soh et al. | |
| 2009/0035838 A1 | 2/2009 | Quake et al. | |
| 2009/0050569 A1 | 2/2009 | Jung et al. | |
| 2009/0220932 A1 | 9/2009 | Ingber et al. | |

OTHER PUBLICATIONS

International Search Report and Written Opinion of the International Searching Authority for International Application No. PCT/US2010/059270, dated Feb. 8, 2011.
Dittrich et al. "Lab-on-a-chip: microfluidics in drug discovery", 2006, Nat Rev Drug Discovery 5:210-218.
Beyor et al., "Immunomagnetic bead-based cell concentration microdevice for dilute pathogen detection", 2008, Biomed Microdevices 10:909-917.
Kamei et al. "Microfluidic Genetic Analysis with an Integrated a Si:H Detector", 2005, Biomed Microdevices 7:147-152.
Cheong et al., "Gold nanoparticles for one step DNA extraction and realtime PCR of pathogens in single chamber", 2008, Lab Chip 8:810-813.
Ashkin et al., "Optical trapping and manipulation of single cells using infrared laser beams", 1987, Nature 330:769-771.
Chiou et al, "Massively parallel manipulation of single cells and microparticles using optical images", 2005, Nature 436:370-372.
Hughes, "Strategies for dielectrophoretic separation in laboratory-on-a-chip systems", 2002, Electrophoresis 23:2569-2582.
Lee et al. "Microelectromagnets for the control of magnetic nananoparticles", 2001, Appl Phys Lett 79:3308-3310.
Yan et al. "Near-field magnetic-tweezer manipulation of single DNA molecules", 2004, Phys Rev E 70:011905.
Davis et al., "Deterministic hydrodynamics: Taking blood apart", 2006, Proc Natl Acad Sci USA 103: 14779-14784.
Dufresne et al., "Optical tweezer arrays and optical substrates created with diffractive optics", 1998, Rev Sci Instrum 69: 1974-1977.
Kremser et al., "Capillary electrophoresis of biological particles: Viruses, bacteria, and eukaryotic cells", 2004, Electrophoresis 25:2282-2291.
Cabrera et al., "Continuous concentration of bacteria in a microfluidic flow cell using electrokinetic techniques", 2001, Electrophoresis 22:355-362.
Liu et al., "Evidence for Localized Cell Heating Induced by Infrared Optical Tweezers", 1995, Biophys J. 68:2137-2144.
Ashkin et al., "Optical Trapping and Manipulation of Viruses and Bacteria", 1987, Science 235:1517-1520.
Applegate et al., "Optical trapping, manipulation, and sorting of cells and colloids in microfluidic systems with diode laser bars", 2004, Optical Express 12:4390-4398.
Pethig et al., "Applications of dielectrophoresis in biotechnology", 1997, Trends Biotechnol 15:426-432.
Menachery et al., "Controlling cell destruction using dielectrophoretic forces", 2005, NanoBiotechnology 152:145-149.
Muller et al., "The Potential of Dielectrophoresis for Single-Cell Experiments", 2003, IEEE Eng Biol Med Mag: 22: 51-61.
Sebastian et al., "Formation of multilayer aggregate of mammalian cells by dielectrophoresis", 2006 J. Micromech Microeng 16: 1769-1777.
Gijs, "Magnetic bead handling on-chip: new opportunities for analytical applications", 2004, Microfluidics Nanofluidics 1:22-40.
Davis et al., "Deterministic hydrodynamics: Taking blood apart", 2006, Proc Natl Acad Sci USA 103: 1779-1784.
Kim et al, "Synthesis of ferrofluid with magnetic nanoparticles by sonochemical method for MRI contrast agent", 2005, J Magn Magn Mater 289:328-330.

(56) References Cited

OTHER PUBLICATIONS

Scherer et al., "Ferrofluids: Properties and Applications", 2005, Brazilian J Phys 45:718-727.
Kashevsky, "Nonmagnetic particles in magnetic fluid: Reversal dynamics under rotating field", 1997, Phys Fluids 9:1811-1818.
Rosensweig Re (1997) Ferrohydrodynamics (Dover, New York).
Odenbach S (2002) Ferrofluids: Magnetically Controllable Fluids and Their Applications (Springer, New York).
Yellen et al. "Arranging matter by magnetic nanoparticle assemblers", 2005, Proc Natl Acad Sci USA 102:8860-8864.
Mao et al., "Towards ferrolluidics for µ-TAS and lab on-a-chip applications", 2006, Nanotechnology 17:34-47.
Zahn et al., "Ferrohydrodynamic pumping in spatially uniform sinusoidally time-varying magnetic fields", 1995, J of Magnetism and Magnetic Materials 149: 165-175.
Happel, J., Brenner H (1983) "Low Reynolds Number Hydrodynamics".
Goldman et al, "Slow viscous motion of a sphere parallel to a plane wall-I Motion through a quiescent fluid", 1967, Chem Eng Sci 22:637-651.
Ise, "When, why, and how does like like like"—Electrostatic attraction between similarly charged species- 2007, Proc Jpn Acad B Phys Biol Sci 83:192-198.
Massart, "Preparation of Aqueous Magnetic Liquids in Alkaline and Acidic Media", 1981, IEEE Trans Magn 17:1247-1248.
Fischer et al, "Ferro-microfluidic device for pathogen detection", 2008, IEEE Int Conf on Nano/Micro Eng and Molecular Syst China, 907-910.
Maiorov, "Exerimental Study of the Permeability of a ferrofluid in an alternating magnetic field", 1979, Magnetohydrodynamics 15:135-139.
Horan et al., "Stable cell membrane labeling", 1989, Nature 340: 167-168.
Green, The Sigma-Aldrich Handbook of Stains, Dyes & Indicators, Aldrich Chemical Co. (Milwaukee, WI): 1990, 721-722.
Bautista et al., "Comparative study of ferrofluids based on dextran-coated iron oxide and metal nanoparticles for contrast agents in magnetic resonance imaging", 2004 Nanotechnology 15: S154-S159.
Tung et al., "Magnetic properties of ultrafine cobalt ferrite particles", (2003) J Appl Phys 93: 7486-7488.
Blattner et al., "The complete genome sequence of *Escherichia coli* K-12" 1997, Science 277:1453-1474.
Lekka et al, "Elasticity of normal and cancerous human bladder cells studies by scanning force microscopy", 1999, Eur Biophys J 28: 312-316.
Leidong Mao et al. "Towards ferrofluidics for [mu]-TAS and lab on-a-chip applications; Towards ferrofluidics for mu-TAS and lab on-a-chip applications", Nanotechnology, IOP Bristol, GB, vol. 17, No. 4, Feb. 28, 2006, pp. s34-s47.
Kose, A.R., "Label-free cellular manipulation and sorting via biocompatible ferrofluids", Proc. Natl. Acad. Sci USA., Dec. 22, 2009, vol. 106, No. 51, pp. 21478-21483.
Kose, et al., "Supporting Information to Label-free Cellular Manipulation and Sorting via Biocompatible Ferrofluids," Proceedings of the National Academy of Sciences, USA, Dec. 7, 2009, Retrieved from the Internet: http://www.onas.org/content/suppl/2009/12/07/0912138106.DCSupplemental/Appendix_PDF.pdf(Retrieved Dec. 4, 2017).

* cited by examiner

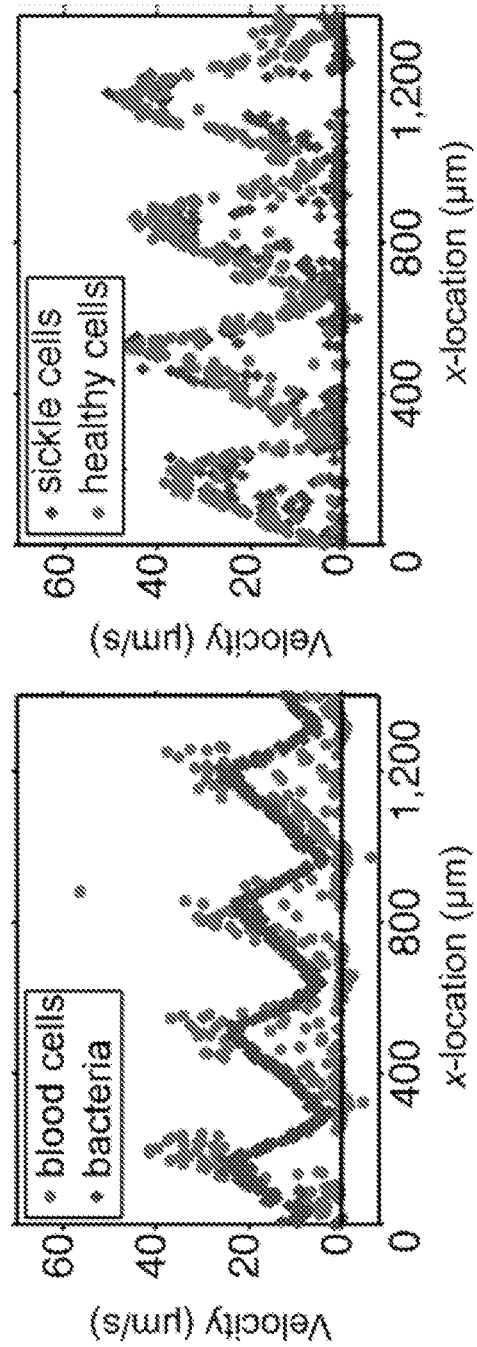

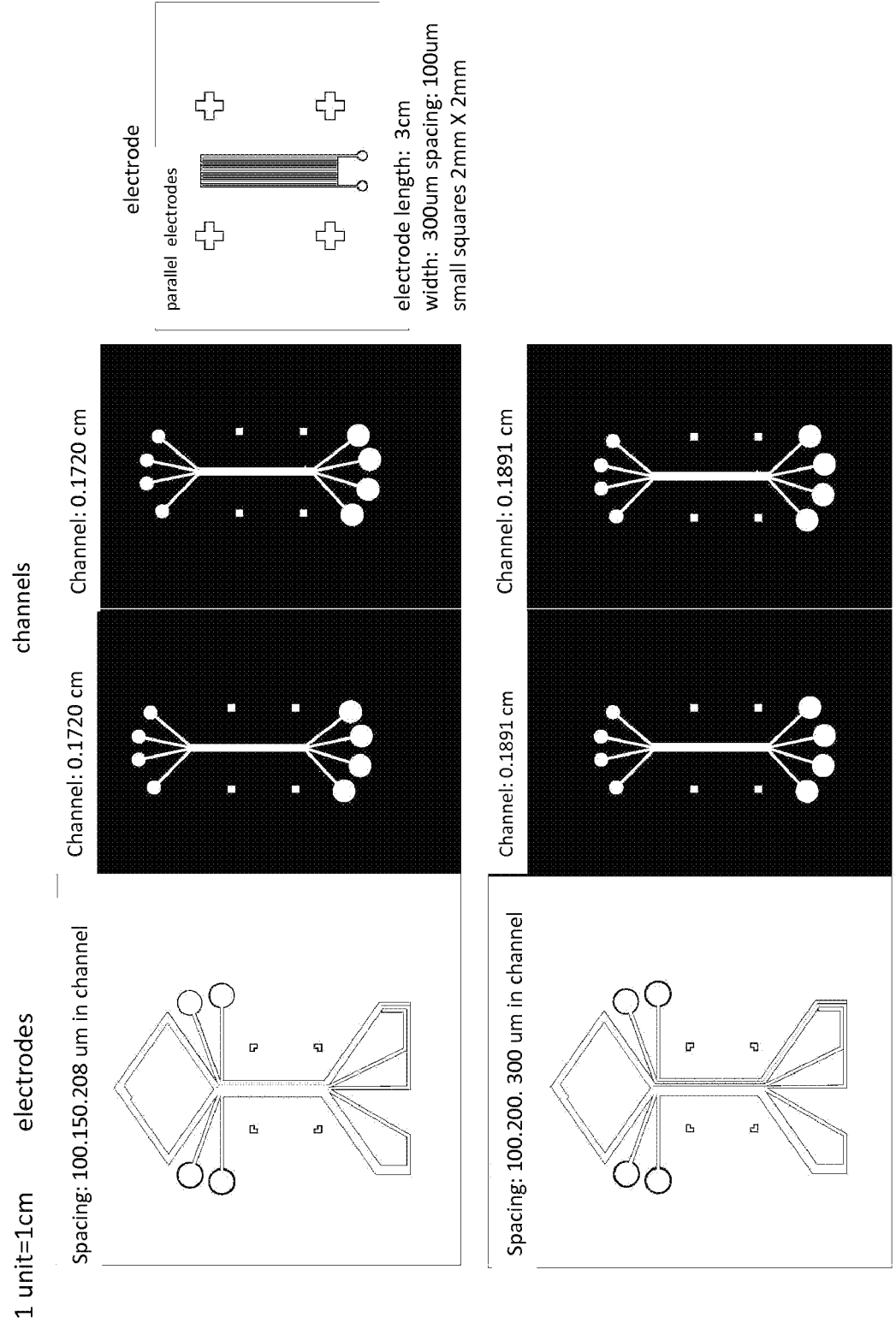

LABEL-FREE CELLULAR MANIPULATION AND SORTING VIA BIOCOMPATIBLE FERROFLUIDS

BACKGROUND OF THE INVENTION

Early diagnosis of diseases involving rare cells in blood (such as metastatic cancer or low-level bacteremia) and accurate monitors of certain genetic conditions (such as sickle cell anemia) require rapid and accurate separation, sorting, and direction of target cell types toward sensor surface. In that regard, cellular manipulation, separation, and sorting are increasingly finding application potential within various bioassays so the context of cancer diagnosis (Dittrich et al., 2006: *Nat Rev Drug Discovery* 5:210-218), pathogen detection (Beyor et al., 2008, *Biomed Microdevices* 10:909-917), and genomic testing (Kamei et al. 2005, *Biomed Microdevices* 7:147-152; Cheong el al., 2008, *Lab Chip* 8:810-813).

A variety of contactless micromanipulation methods exist, including optical tweezers (Ashkin et al., 1987, *Nature* 330:769-771; Chiou et al., 2005, *Nature* 436:370-372), dielectrophoresis (DEP) (Hughes, 2002, *Electrophoresis* 23:2569-2582), magnetic bead-based separators (Lee et al., 2001, *Appl Phys Lett* 79:3308-3310; Yan et al., 2004, *Phys Rev E* 70:011905), and deterministic hydrodynamics (Davis et al., 2006, *Proc Natl Acad Sci USA* 103:14779-14784). However, most existing methods have been unable to reliably achieve fast speed, high throughput and resolution, simultaneously with low costs (Dufresne et al., 1998, *Rev Sci Instrum* 69:1974-1977; Kremser et al., 2004, *Electrophoresis* 25:2282-2291; Cabrera et al., 2001 *Electrophoresis* 22:355-362). Optical tweezers offer high resolution and sensitivity for manipulating single cells, although such manipulation may cause sample heating (Liu et al., 1995, *Biophys J* 68:2137-2144), and is typically limited to a very small area (Ashkin et al., 1987, *Science* 235:1517-1520). Holographic schemes have recently extended the reach of optical tweezers to several tens of cells simultaneously (Applegate et al., 2004, *Optical Express* 12:4390-4398), although the overall throughput remains quite low. Schemes based on electric fields, such as DEP, offer the potential to realize integrated, cost-effective devices for the simultaneous manipulation of multiple cells; nevertheless, their performance depends sensitively on the electrical properties of the specific liquid medium, the particle shape, and its effective dielectric constant (Pethig et al., 1997, *Trends Biotechnol* 15:426-432). DEP device operating regimes and the working ionic medium need to be carefully optimized for each different cell type so as to reach workable compromise between the need to reduce heating (Menachery et al., 2005, *NanoBiotechnology* 152:145-149; Muller, et al., 2003, *IEEE Eng Biol Med Mag* 22:51-61) and minimize cell polarization (Sebastian et al., 2006, *J Micromech Microeng* 16:1769-1777). Using functionalized magnetic beads to separate target molecules and cells overcomes these challenges through the use of magnetic fields instead of electric. However, the downside of this technique is the lengthy incubation time and wash cycles, and the difficulty of removing the label post priori (Gijs 2004, *Microfluidics Nanofluidics* 1:22-40). The deterministic hydrodynamics approach, as demonstrated by Davis et al. (Davis et al., 2006, *Proc Natl Acad Sci USA* 103:14779-14784), is capable of achieving high resolution of separation without the use of any electromagnetic fields. However, high throughput with this device requires high-resolution lithography on a large area, keeping the cost per device high.

Most common applications of ferrofluids in biomedicine involve highly dilute colloidal suspensions of magnetic nanoparticles. Their widest commercial use is as MRI contrast agents (Kim et al., 2005, *J Magn Magn Mater* 289:328-330). When properly coated with targeting antibodies, they can also be used in hyperthermia therapy for cancer or as sensors to detect pathogens (Scherer et al., 2005, *Brazilian J Phys* 45:718-727). While these advances in the use of ferrofluids provide many opportunities in medicine and diagnostics, there remains a need in the art for a microfluidic platform that uses biocompatible ferrofluids for the controlled manipulation and rapid separation of both microparticles and live cells. The present invention satisfies this need.

SUMMARY OF THE INVENTION

A device for separating a sample of particles suspended in a biocompatible ferrofluid is described. The device includes a microfluidic channel having a sample inlet, at least one output, and a length between the sample inlet and the at least one output, wherein a sample can be added to the sample inlet and flow along the length to the at least one outlet. The device includes a plurality of electrodes, wherein the microfluidic channel length transverses the plurality of electrodes, and further includes a power source for applying a current to the plurality of electrodes to create a magnetic field pattern along the length of the microfluidic channel. In one embodiment, the spacing between electrodes is gradually increased. In another embodiment, the spacing between electrodes is gradually decreased. In another embodiment, the plurality of electrodes comprise at least one electrode layer. In another embodiment, the plurality of electrodes comprises a plurality of electrode layers. In another embodiment, the plurality of electrode layers is in a substantially orthogonal pattern. In another embodiment, the plurality of electrodes comprises a pattern of concentric circles. In another embodiment, the walls of the microfluidic channel length include a pocketed, a ridged, a grooved, a trenched or a sloped region. In another embodiment, the microfluidic channel length transverses at least a portion of the plurality of electrodes at an angle between about 1-90 degrees. In another embodiment, the particles are living cells.

Also described is a system for separating at least one target from a sample suspended in a biocompatible ferrofluid. The system includes a microfluidic channel having a sample inlet, at least one output, and a length between the sample inlet and the at least one output, wherein a sample can be added to the sample inlet and flow along the length to the at least one outlet. The system also includes a plurality of electrodes, wherein the microfluidic channel length transverses the plurality of electrodes, and further generates a magnetic field pattern along the length of the microfluidic channel when a current is applied to the electrodes. The system further includes at least one target in a sample suspended in a biocompatible ferrofluid, wherein the at least one target is separated from the remaining sample as the at least one target passes along at least a portion of the microfluidic channel length. In one embodiment, the biocompatible ferrofluid comprises a suitable amount of ionic species to control the osmotic pressure on the cells to promote cell sustainability. In another embodiment, the biocompatible ferrofluid comprises a citrate concentration of between about 5-200 mM. In another embodiment, the biocompatible ferrofluid comprises a citrate concentration of about 40 Mm. In another embodiment, the biocompatible ferrofluid has a pH of about 7.4. In another embodiment, the at least one target is separated based on target size. In another embodiment, the at least one target is separated based on target shape. In another embodiment, the at least one target is separated based on target elasticity. In another embodiment, the target is separated by being directed to a selected outlet. In another embodiment, the target is trapped based on the spacing of electrodes. In another embodiment, the at least one target is a cell. In another embodiment, the at least one target is a particle.

Also described is a method for separating at least one cell type. The method includes the steps of suspending two or more cell types in a biocompatible ferrofluid to form a sample, passing the sample through a microfluidic channel that transverses a plurality of electrodes, applying a current to the plurality of electrodes to create a magnetic field pattern along the length of the microfluidic channel, and sorting the cells into at least one output channel based on a variation of at least one of cell size, shape and elasticity. In one embodiment, the cells are separated at an efficiency of at least about 90%. In another embodiment, the size resolution is separating is less than about 10 μm. In another embodiment, the cells are separated in less than about 1 minute.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A is a schematic of the experimental setup displaying the microfluidic channel and the underlying electrodes (not drawn to scale). Two output channels from an amplifier provide sinusoidal currents ($I_1$ and $I_2$) phase-locked 90° with respect to each other. The neighboring electrodes on the substrate are connected in a manner to carry sinusoidal currents in quadrature and support a traveling wave magnetic field within the microfluidic channel. The magnetic field gradient generated pushes the nonmagnetic microspheres or cells within the ferromicrofluidic channel up and into the gap between electrodes (i); the traveling field also causes the cells to rotate and roll along the channel ceiling, resulting in continuous translation along the length of the channel at frequencies above a threshold (ii). The resulting microparticle motion is observed with an upright microscope from above and captured with a CCD camera at 18 frames per second for further analysis. FIG. 1B depicts a COMSOL simulation of a magnetic field (dark arrows) and magnitude of magnetic flux density (color) across the cross-section of the ferromicrofluidic device at a given instant in time. Fainter arrows depict the field at ever 30° within one period. Simulation is for 12-A peak-to-peak current input at 1,670 Hz. FIG. 1C is a graph of computed force and torque on a 6-μm diameter microsphere along the length of the microchannel with 7-A peak-to-peak input excitation at 4.6 kHz. FIG. 1D is a graph of computed magnetic force and torque as a function of frequency for the same particle located between electrodes on the channel ceiling. Input current amplitude is 7 A peak to peak; assumed slip factor for all simulations depicted here is 1.

FIG. 2, comprising FIGS. 2A-2C characterizes biocompatible ferrofluid.

FIG. 3, comprising FIG. 3A (middle) is a spatial distribution of instantaneous average x-velocities for 6-μm-diameter particles at 7-A input current amplitude (peak to peak) at two different frequencies. Because of repulsive forces from magnetic field gradients, microparticles either slow down or completely stop in between electrodes. Zero crossings with negative slope correspond to stable equilibrium points (i.e., particle trapping); FIG. 3A (top) shows at 10 Hz, particle trajectories terminate in between electrodes, resulting in trapping. FIG. 3A (bottom) shows at 4,640 Hz, particles move continuously throughout the length of the channel. This is the regime where magnetic torque from the locally rotating component of the traveling wave dominates over the repulsive forces. The black dots at the end of each trajectory indicate where particles eventually stop. FIG. 3B shows that above a critical frequency ($f_c$), the 6-μm microspheres roll continuously along the top channel surface without getting trapped.

FIG. 4, comprising FIG. 4A depicts the particle size dependence of critical frequency ($f_c$). Discrete $f_c$ values for different diameters of particles enable size-based separation by tuning to the right frequency. The solid curve corresponds to the simulation result with a slip factor of 1 and a particle-wall gap of 1 nm. FIG. 4B depicts the average manipulation speed as a function of input frequency for two different particle sizes; 2.2- and 9.9-μm particles can be separated at 400 Hz. FIG. 4C is a fluorescent microscopy image from a section of the microfluidic channel containing 2.2- and 9.9-μm microspheres randomly dispersed within the channel right before the excitation. Vertical lines indicate electrode borders. FIG. 4D is a snapshot of the channel from the same location as in FIG. 4C, 45 seconds after the excitation (6 A peak to peak, 400 Hz) is turned on. The 9.9-μm particles quickly localize within the nearest spring between electrodes, whereas 97% of the 2.2-μm microspheres continuously travel from right to left without being trapped. Almost all of the smaller microspheres within the field of view in FIG. 4D have entered from the right as a fresh batch.

FIG. 5, comprising FIGS. 5A and 5B, depict cellular separation with bacteria and blood cells. FIG. 5A depicts the spatial distribution of x-velocities at 200 Hz in a sample containing *E. coli* bacteria and red blood cells. At this frequency, most red blood cells are trapped between the electrodes (indicated by their zero local speeds), whereas *E. coli* can slowly but continuously move through that region. Fluctuations in the red blood cell data are statistical in nature, as explained herein. FIG. 5B depicts sickle cell separation. Sickle cells, which have an elongated shape and altered elasticity compared with normal red blood cells, are trapped and concentrated between the electrodes, whereas the healthy cells are still able to circulate within the microfluidic channel at 300 Hz. Electrode spacing of the device in FIG. 5A is different from that in FIG. 5B, resulting in different $f_c$ s for red blood cells within each channel.

FIG. 6, comprising FIGS. 6A-6C.

FIG. 7, comprising FIGS. 7A and 7B depict alternative embodiments of the electrode and channel components of the separating device. FIG. 7A depicts electrode formations of 100, 150, 200 and 300 µm spacing in the channel. FIG. 7B depicts channel formations of between about 0.17-0.19 cm, and having four inlets and four outlets.

FIG. 8, comprising FIG. 8A depicts a multi-layer electrode pattern that is substantially orthogonal FIG. 8B depicts electrodes in a pattern of concentric circles.

DETAILED DESCRIPTION

Figure 1A:
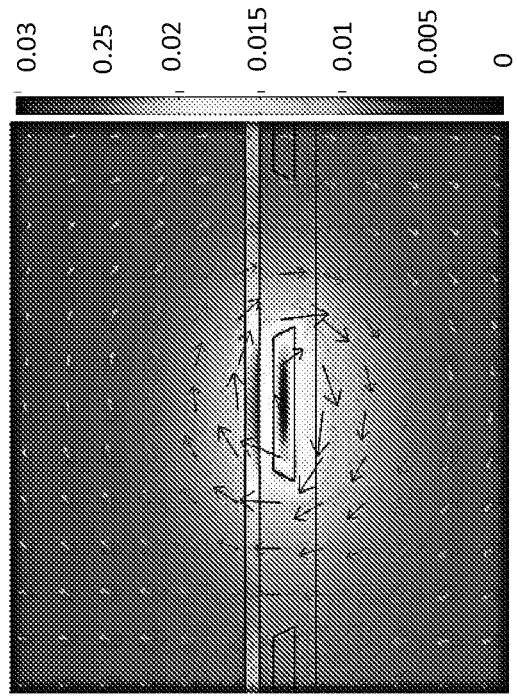
FIGS. 1A-1D, illustrate a ferromicrofluidic device and particle manipulation platform.

The present invention relates to a microfluidic platform that uses biocompatible ferrofluids for the controlled manipulation and rapid separation of both microparticles and live cells. More particularly, the present invention relates to the high-throughput manipulation, label-free sorting and separating of cells via a concentrated ferrofluid that is bio-compatible. Bio-compatibility of the ferrofluid is based on an effective balance, or concentration, of ionic surfactant such as citrate. Bio-compatibility generally requires a neutral pH, a sufficient osmotic pressure on the cells, and a stable ferrofluid (too much ionic content destabilizes the suspension). This low-cost platform exploits differences in particle size, shape, and elasticity to achieve rapid and efficient separation. Using microspheres, size-based separation is demonstrated with about separation efficiency and sub-10-µm resolution in less than about 45 seconds. The present invention also provides for the continuous manipulation and shape-based separation of live red blood cells from sickle cells and bacteria. These demonstrations highlight the ability of ferromicrofluidics to significantly reduce incubation times and increase diagnostic sensitivity in cellular assays through rapid separation and delivery of target cells to sensor arrays.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Throughout this disclosure, various aspects of the invention can be presented range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Separation Systems and Devices

In one aspect, the present invention includes a microfluidic system, based on ferrohydrodynamics for the label-free manipulation and separation of cells and microorganisms within biocompatible ferrofluids. In one embodiment, the system includes a water-based ferrofluid is used as a uniform magnetic environment that surrounds the cells or other particles within a microfluidic channel. Cells and other nonmagnetic particles within the ferrofluid act as "magnetic voids" (Kashevsky, 1997, *Phys Fluids* 9:1811-1818), in a manner analogous to electronic holes in a semiconductor. An externally applied magnetic field gradient can attract magnetic nanoparticles, which causes nonmagnetic microparticles or cells to be effectively pushed away (Rosensweig R E (1997) *Ferrohydrodynamics* (Dover, N.Y.); Odenbach S (2002) *Ferrofluids: Magnetically Controllable Fluids and Their Applications* (Springer, N.Y.)). Recently, this principle has been applied to capture nonmagnetic microbeads between magnetic film islands in a microchannel filled with ferrofluid (Yellen et al., 2005, *Proc Natl Acad Sci USA* 102:8860-8864). In contrast to this, the present invention can utilize a microfluidic device with integrated copper electrodes that carry currents to generate programmable magnetic field gradients locally, as depicted in FIG. 1A.

Figure 8A:
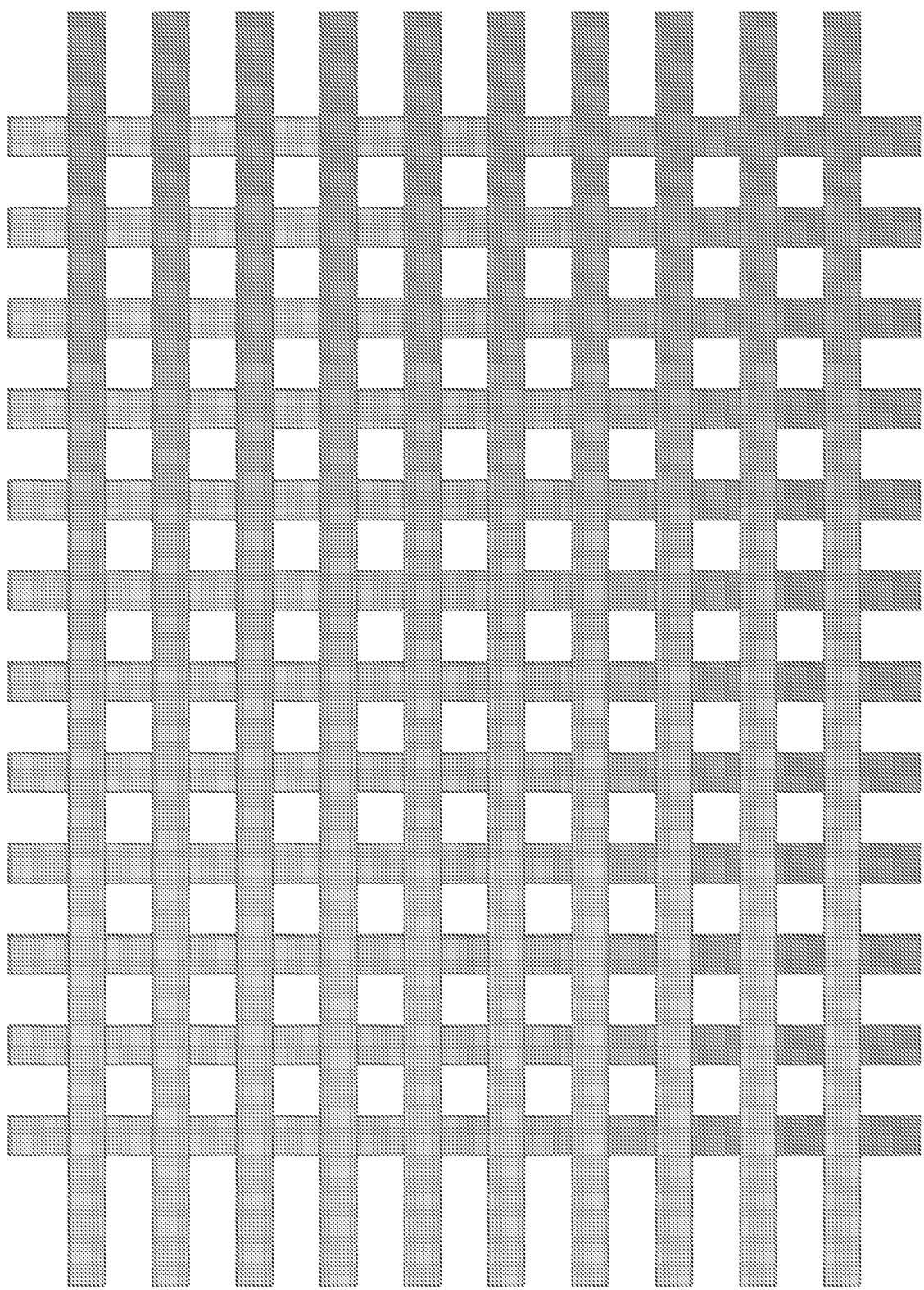
FIGS. 8A and 8B, depict alternative embodiments of electrode patterns.
Figure 8B:
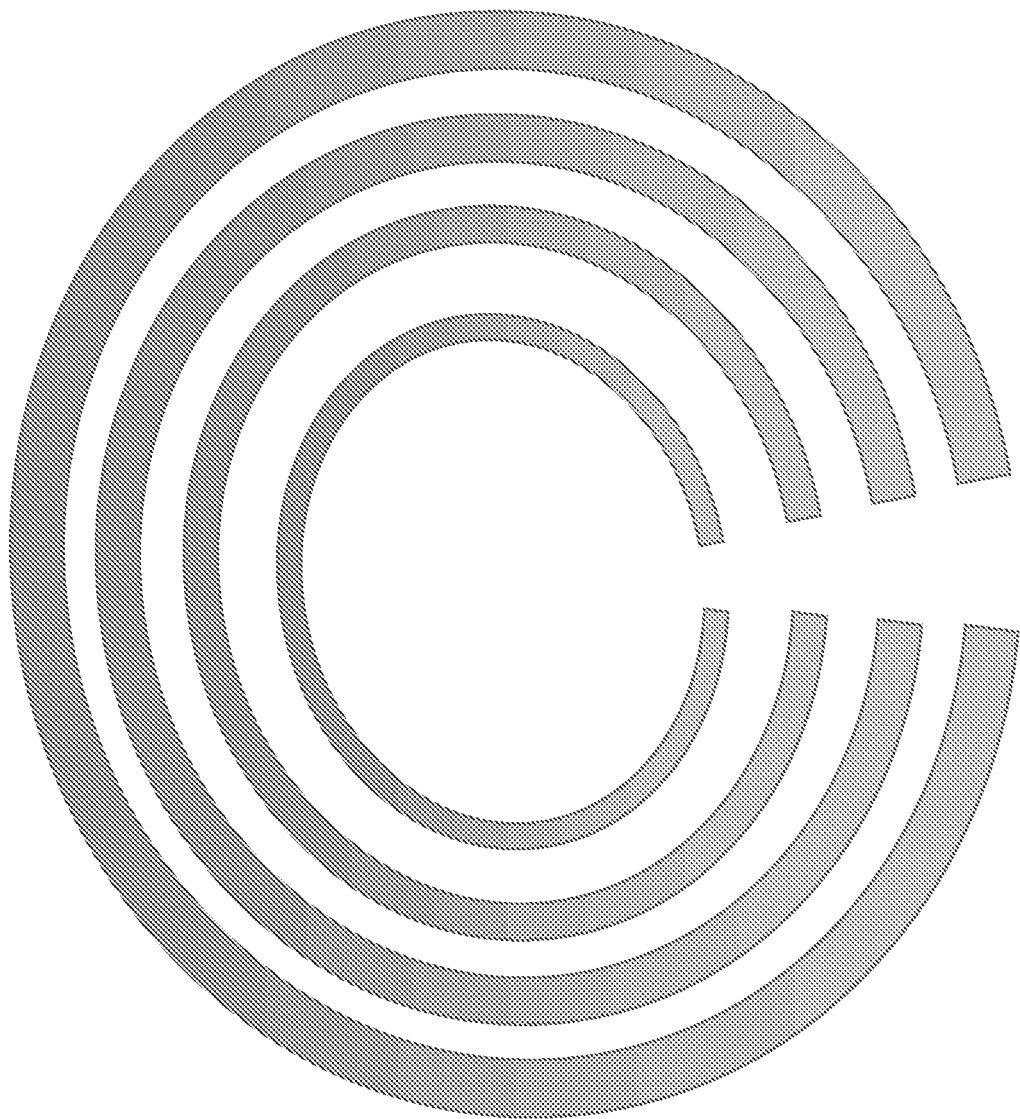

For example, the particle manipulation device of the present invention includes two primary components; 1) a microfluidic channel; and 2) underlying electrodes. At least one electrode layer may sit atop a standard, insulated metal substrate. For example, an aluminium substrate coated with an insulating polymer may be used, which allows efficient heat sinking, and enable AC currents up to 10 A at low voltages through the electrodes. In one exemplary embodiment, a single electrode layer is used, as may be seen in FIG. 1A. In other exemplary embodiments, multiple electrode layers are used to provide multi-dimensional control, for example, such as the orthogonal electrode layers depicted in FIG. 8A. Within a given electrode layer, the electrodes may be about 30 μm high, about 300 μm wide and about 2 cm in length. In alternative embodiments, the electrodes within a given layer may range anywhere from about 5-100 μm high, about 0.01-1 mm wide, and about 0.1-10 cm in length, and any whole or partial increments therebetween. Thus, it should be appreciated that the size of electrodes utilized is not limited, and can vary across multiple electrode layers. Further, the electrodes may include any area shape, curvature or pattern, and may include variable gap sizes between electrodes. For example, FIG. 7A depicts electrode formations of 100, 150, 200 and 300 μm spacing in the channel region. In another exemplary embodiment, a multi-layer, orthogonal pattern may be used, as depicted in FIG. 8A. In yet another exemplary embodiment, a concentric circle electrode pattern may be used, as depicted in FIG. 8B, such that traveling waves effectively move the particles or cells into the circles, out of the circles, or trap them in various portions of the circles. In yet another exemplary embodiment, the electrodes may be "wiggly", or generally non-linear, so as to introduce disturbance forces and torques on nearby particles or cells. These wiggly regions may be uniform, non-uniform, random and/or periodic in nature throughout the electrodes. Again, it should be appreciated that the shape, spacing and pattern of electrodes may vary within a given electrode layer, and may further vary across multiple layers, such that any combination of shape, size, spacing and patterning may occur with an electrode layer and across multiple layers to create the desired magnetic field. The electrodes may be composed of any suitable conductive material, such as copper as would be understood by those skilled in the art. The electrodes can be fabricated by wet etching the copper layer of a thermal-clad printed circuit board (on an insulated metal substrate) through a photoresist mask. It should be appreciated that any type of etching or other suitable fabrication method may be used in creation of the electrodes, as would be understood by those skilled in the art.

The channel can include at least one inlet and at least one outlet, and may run at an angle such that the channel ultimately transverses the electrodes. For example, in one embodiment, the microfluidic channel can be rotated by about 90 degrees so that the electrodes of the device are substantially parallel to its length. In other embodiments, the channel transverses the electrodes at an angle between about 1-90 degrees, and any whole or partial increments therebetween. In a further exemplary embodiment, the channel transverses the electrodes in a substantially straight line. In still other exemplary embodiments, the channel transverses the electrodes in a curved, bent or generally non-linear pattern. The microfluidic channel can range from 20-100 μm, 1-3 mm wide and 2-3 cm in length, and any whole or partial increments therebetween. In other exemplary embodiments, the channel may include any number and size of pockets, ridges, grooves, trenches, and/or slopes within the channel walls, such that the particles or cells traveling within the channel can be locally concentrated or dispersed, based on the conformational effects of the contours of the channel walls. Additional exemplary channels, having multiple inlets and outlets, are depicted in FIG. 7B. The channels may be composed of any suitable material as would be understood by those skilled in the art. In one embodiment, the channel may be prepared from polydimethylsiloxane (PDMS) stamps through soft lithography, and bonded to an insulating layer of very thin PDMS covering the electrodes (Mao et al., 2006, *Nanotechnology* 17:34-47). In certain embodiments, the channel height may be selected to be well below the optimum for localized ferrohydrodynamic flow, in order to minimize its potential effects on particle migration. While not required, the channel can be washed with a 1% triton-X solution for about 10 minutes before introducing the ferrofluid/microsphere mixture into the microfluidic device, to minimize particle attachment to the PDMS walls. It should be appreciated that the substrate, insulating layer and channel can each alternatively be composed of materials having similar features and/or properties, as would be understood by those skilled in the art. Thus, the devices of the present invention can be constructed on an inexpensive printed circuit board that features an insulated copper layer etched via a single, low-resolution transparency mask to define the electrodes. The microfluidic channel can be constructed via soft lithography using a low-resolution mold. In certain embodiments, device fabrication does not necessitate a clean room, and hence, can be fabricated rapidly and inexpensively.

Figure 1B:
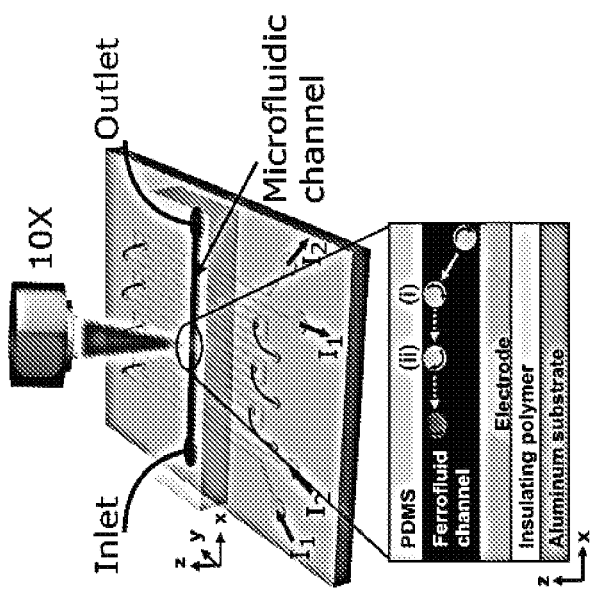

A travelling magnetic field may be generated within the channel from a power source by applying current to the electrodes to create a magnetic field pattern along the length of the microfluidic channel. Alternating currents up to about 7 A peak to peak in amplitude and with frequencies from about 10 Hz to 100 kHz, which correspond to a maximum magnetic field strength of about 90 Oe within the ferrofluid, can be applied to the electrodes. In other exemplary embodiments, the generated magnetic field strength may range between 1-200 Oe, and any whole or partial increments therebetween. In one example, the magnetic field is generated by applying alternating currents in quadrature to a single layer of electrodes, to create a periodic magnetic field pattern that travels along the length of the microchannel. With this configuration, the device is able to create both magnetic field gradients, resulting in a time-average force on the cells or particles, and local rotation of ferrofluid magnetization, which eventually results in torque on the nonmagnetic particles, as illustrated in FIG. 1B.

Figure 1C:
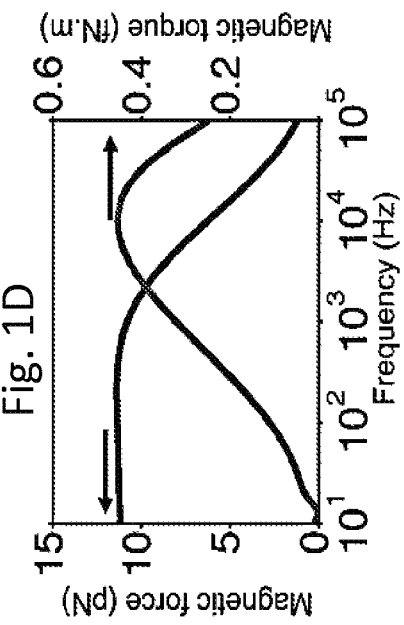
Figure 1D:
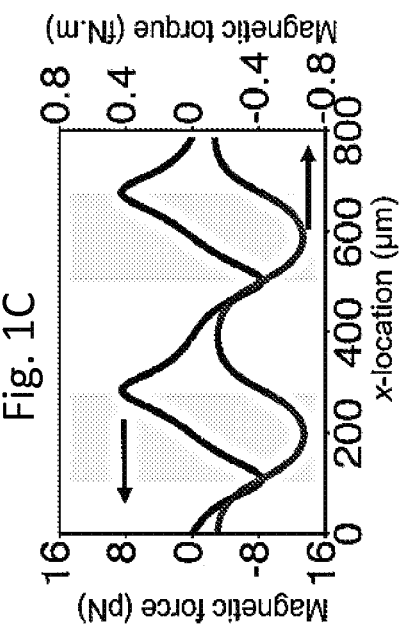

When the current is turned on, the cells or particles are pushed away from the electrodes to the top of the channel, due at least in part to magnetic force, where they start to rotate and roll along its length, due at least in part to magnetic torque. The device behavior can thus mimic the frequency-dependent susceptibility of the particular ferrofluid used. For a given particle size, its speed may depend on the local force and torque values along the channel length, as illustrated in FIG. 1C. For example, at low frequencies, the force dominates, pushing the nonmagnetic microparticles up to the channel ceiling and into the space between the electrodes. In another example, at high frequencies, the rolling microparticles can overcome the diminishing repulsion caused by magnetic force and move continuously along the channel, as illustrated in FIG. 1D.

Using the aforementioned microfluidic setup, the typical magnetic force that can be applied on a particle several micrometers in diameter can be on the order of tens of piconewtons, which is significantly larger than what is typical with optical tweezers on μm-size particles. In certain embodiments, this actuation force can be increased by applying larger excitation currents. For example, a simple heat sink can maintain the channel contents at room temperature up to 10-A peak-to-peak input current (Mao L, Koser H (2006) Toward ferrofluidics for μ-TAS and lab on-a-chip applications. *Nanotechnology* 17:34-47).

Biocompatible Ferrofluids

Ferrofluids are colloidal mixtures of nanometer sized magnetic particles, such as cobaltferrite, covered by a surfactant, suspended in a carrier medium that is compatible with the surfactant material. For example, a sample reaction that results in magnetite particles is as follows:

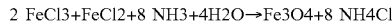

A 10% by volume suspension of magnetite has a saturation magnetization of around 560 G. The magnetization of each single-domain particle responds to a high magnetic field with a time constant on the order of 10 μs. High magnetic field gradients can be used to position the ferrofluid. "Spikes" and other interesting features may appear at the ferrofluid surface in the presence of such high fields.

In one embodiment, particle diameters can range from about 1 nm to about 100 nm, and any whole or partial increments therebetween. For example, end without limitation, the particle diameters can range between 1-10 nm, 1-20 nm, 5-50 nm, or 10-100 nm. In a preferred embodiment, particle diameters average about 10 nm. Volume fractions may range from 0.1% to about 10%, and any whole or partial increments therebetween.

In another embodiment, the ferrofluids of the present invention are biocompatible and can sustain live cells for several hours without deterioration in physical properties or sustainability, allowing for extended examination of the target sample. The biocompatible ferrofluid can be suitable for sustaining any living cell type and/or shape, such as any animal or plant tissue cell type, any microorganism, or any combination thereof, for example. Of course, the ferrofluid is also suitable for suspending any type of particle, and for any sized or shaped particle, or particle is clusters or clumps, whether living or non-living.

Citrate is an effective surfactant in ferrofluids, and it is mostly biocompatible in cell cultures as well. Therefore, in one embodiment, citrate was utilized both to stabilize the ferrofluid and to provide an ionic medium for the cells to survive in. In this context, determining a novel and optimum citrate concentration was necessary, as too little or too much citrate would result in particle aggregation and precipitation within the ferrofluid. Further, cell survival within the ferrofluid depends on having enough ionic species to control the osmotic pressure on the cells to promote sustainability. In one exemplary embodiment, a citrate concentration within the ferrofluid resulting in a stable colloidal suspension of magnetic nanoparticles was about 40 mM. While higher citrate concentrations might begin to gradually destabilize the ferrofluid, concentrations of citrate may range anywhere between 5-200 mM, and any whole or partial increments therebetween, depending on the characteristics and type of ferrofluid used. In the exemplary embodiment depicted in FIG. 2C, it was also determined that the minimum concentration of citrate, stabilized with citric acid to result in a pH of about 7.4, that first resulted in substantial cell survival over the course of several hours was about 40 mM. At this ionic concentration, the cells were viable and the ferrofluid was stable. Hence, in a preferred embodiment, a citrate concentration of about 40 mM can be used as effective biocompatible ferrofluid. As contemplated herein, and depending on the type of ferrofluid used, the ferrofluids of the present invention may also be stabilized at pH ranges from between about 2-11, and any whole or partial increments therebetween. In certain embodiments, the ferrofluid is biocompatible, such that cells can survive within the ferrofluid for at least about 1 hour, about 2 hours, about 3 hours, about 5 hours, about 10 hours, and even up to about 24 hours.

Calculations for Particle Manipulation

Provided herein is an analytical approach that enables the estimation of particle velocities and critical frequencies observed in the ferromicrofluidic devices of the present invention. To simplify the calculations, a perfectly spherical, incompressible microparticle, a magnetically linear ferrofluid, and a slip factor (see below) that is independent of field magnitude and frequency are assumed. Further assumed is that the spherical particle radius (R) is small compared to the wavelength of the travelling magnetic field ($\vec{H}$)—as determined by electrode dimensions and spacing, so the $R|\nabla \vec{H}| \ll |\vec{H}|$ holds true. Under these assumptions, the ferrofluid magnetization in the immediate vicinity of the microparticle—and, the virtual magnetization ($M_{eff}$) within the particle's volume ($V_p$)—can be approximated as uniform. It is also approximated that any field value (but not its gradient) is constant within the interior extent of the microparticle.

The total instantaneous force on that dipole is then given by $$\vec{F}_{ins} = \int_{V_p} \nabla(\vec{M}_{eff} \cdot \vec{B}_{in}) dV \qquad (1)$$

where $B_{in}$ is the magnetic flux density within the spherical microparticle and the integration is over the internal volume of the particle (Zahn et al., 1995, *J of Magnetism and Magnetic Materials* 149:165-173). Under these assumptions, the surface terms in (1) due to discontinuities in M and B create pressure terms that integrate out to 0, and a simple vector expansion of the integrand reveals that this term is the same as the Kelvin force density. Hence, the instantaneous force expression can be simplified to $$\vec{F}_{int} = V_p \nabla(\vec{M}_{eff} \cdot \vec{B}_m) \qquad (2)$$

To obtain an eventual analytical expression for the magnetic force, it is helpful to express $M_{eff}$ and $B_{in}$ in terms of the external magnetic field ($H_{ext}$) in the absence of the microparticle, since this field value can be easily obtained from simple simulations. The net magnetization of the particle with a magnetic permeability $\mu_p$ (essentially $\mu_0$) within the ferrofluid (with a complex, frequency-dependent permeability $\mu_f = \mu_0(1+\chi_f)$) depends on $H_{ext}$ as follows $$\vec{M}_{eff} = 3\left(\frac{\mu_p - \mu_f}{\mu_p + 2\mu_f}\right)\vec{H}_{ext} \Rightarrow \vec{M}_{eff} = \frac{-3\chi_f}{3+2\chi_f}\vec{H}_{ext} \qquad (3)$$

Determining the magnetic flux density field within the particle requires consideration of the demagnetization field inside it. The overall field inside the particle is $\vec{H}_{in} = \vec{H}_{ext} - \vec{H}_{dmag}$, with $\vec{H}_{dmag} = \vec{M}_{eff}/3$ for a sphere. Hence, in the linear regime where particle magnetization can be written as $\vec{M}_{eff} = \chi_{eff}\vec{H}_{in}$, one finds $$\frac{\vec{M}_{eff}}{\chi_{eff}} = \vec{H}_{ext} - \frac{\vec{M}_{eff}}{3} \Rightarrow \vec{M}_{eff} = \left(\frac{3\chi_{eff}}{3+\chi_{eff}}\right)\vec{H}_{ext} \qquad (4)$$

Comparing (3) and (4) reveals the effective susceptibility of the particle in terms of the ferrofluid susceptibility:

$$\chi_{\text{eff}} = \frac{-\chi_f}{1+\chi_f} \quad (5)$$

Note that the effective magnetic susceptibility depends on that of the ferrofluid, since the microparticle responds to magnetic forces only because it displaces ferrofluid and creates a "magnetic hole". In that regard, the magnetic medium in which the hole resides determines the strength of the interactions between that magnetic hole and applied fields. The negative sign in (5) indicates that the effective magnetization of the microparticle is in the opposite direction of the local ferrofluid magnetization under static conditions. While $\chi_{\text{eff}} \approx -\chi_f$ for $\chi_f \ll 1$, the effective susceptibility of the magnetic hole approaches −1 in a strongly magnetisable medium. In effect, using too strong a ferrofluid for microparticle manipulation could be counter-productive.

The instantaneous magnetic, force on the particle can be expressed as $$\vec{F}_{ins} = V_p \nabla (\vec{M}_{\text{eff}} \cdot \vec{B}_{in}) = V_p \mu_0 \vec{\nabla}(\vec{M}_{\text{eff}} \cdot (\vec{H}_{in} + \vec{M}_{\text{eff}})) \quad (6)$$
$$= V_p \mu_0 \vec{\nabla}\left(\vec{M}_{\text{eff}} \cdot \vec{H}_{in} + |\vec{M}_{\text{eff}}|^2\right)$$
$$= V_p \mu_0 \vec{\nabla}\left(|\vec{M}_{\text{eff}}|\frac{|\vec{M}_{\text{eff}}|}{\chi_{\text{eff}}}\cos\theta + |\vec{M}_{\text{eff}}|^2\right)$$
$$= V_p \mu_0 \vec{\nabla}\left(|\vec{M}_{\text{eff}}|^2 \frac{\text{Re}\{\chi_{\text{eff}}\}}{|\chi_{\text{eff}}|^2} + |\vec{M}_{\text{eff}}|^2\right)$$

Here, $\theta$ is the angle between $\vec{M}_{\text{eff}}$ and $\vec{H}_{in}$, given by the angle of the complex susceptibility $\chi_{\text{eff}}$. Using $$\vec{M}_{\text{eff}} = 3\left(\frac{-\chi_f}{3+2\chi_f}\right)\vec{H}_{ext},$$

we get $$\vec{F}_{ins} = V_p \mu_0 \left(\frac{\text{Re}\{\chi_{\text{eff}}\}}{|\chi_{\text{eff}}|^2} + 1\right)\left(\frac{9|\chi_f|^2}{9 + 6\text{Re}\{\chi_f\} + 4|\chi_f|^2}\right)\vec{\nabla}|\vec{H}_{ext}|^2 \quad (7)$$

In the presence of traveling fields, the local magnetic field varies sinusoidally, and the time-average force is just half the maximum value of the instantaneous force:

$$\vec{F}_{ave} = \frac{1}{2}V_p \mu_0 \left(\frac{\text{Re}\{\chi_{\text{eff}}\}}{|\chi_{\text{eff}}|^2} + 1\right)\left(\frac{9|\chi_f|^2}{9 + 6\text{Re}\{\chi_f\} + 4|\chi_f|^2}\right)\vec{\nabla}|\vec{H}_{ext}|^2 \quad (8)$$

Similarly, the instantaneous torque on a magnetic dilpole is given by $$\vec{\tau}_{ins} = s\int_{V_p}(\vec{M}_{\text{eff}} \times \vec{B}_{in})dV \quad (9)$$
$$= sV_p(\vec{M}_{\text{eff}} \times \vec{B}_{in}).$$

(Zahn et al., 1995, *J of Magnetism and Magnetic Materials* 149:165-173). Here, the possibility that the rotation of the nonmagnetic microparticle may be subject to a slip s between 0 and 1 has been allowed for. This slip factor represents the ratio of the torque that a non-magnetic microparticle experiences in the ferro-microfluidic devices of the present invention to the value of the torque that would be felt by an isolated particle of the same size and effective magnetization.

The remaining details of the derivation for magnetic torque mirror those for magnetic force. Substituting for the magnetic flux density, one obtains $$\vec{\tau}_{ins} = sV_p(\vec{M}_{\text{eff}} \times \vec{B}_{in}) = sV_p\mu_0(\vec{M}_{\text{eff}} \times (\vec{H}_{in} + \vec{M}_{\text{eff}})) \quad (10)$$
$$= sV_p\mu_0(\vec{M}_{\text{eff}} \times \vec{H}_{in} + \vec{M}_{\text{eff}} \times \vec{M}_{\text{eff}})$$

Since $\vec{M}_{\text{eff}} \times \vec{M}_{\text{eff}} = 0$ and $\vec{M}_{\text{eff}} = \chi_{\text{eff}}\vec{H}_{in}$, one gets $$\vec{\tau}_{ins} = \hat{y}sV_p\mu_0\left(|\vec{M}_{\text{eff}}||\vec{M}_{\text{eff}}|\frac{|\chi_{\text{eff}}|}{|\chi_{\text{eff}}|^2}\sin\theta\right) \quad (11)$$
$$= \hat{y}sV_p\mu_0 \frac{\text{Im}\{\chi_{\text{eff}}\}}{|\chi_{\text{eff}}|^2}\left(\frac{9|\chi_f|^2}{9 + 6\text{Re}\{\chi_f\} + 4|\chi_f|^2}\right)|\vec{H}_{ext}|^2$$

And time average torque is given by $$\vec{\tau}_{ave} = \hat{y}\frac{V_p}{2}s\mu_0 \frac{\text{Im}\{\chi_{\text{eff}}\}}{|\chi_{\text{eff}}|^2}\left(\frac{9|\chi_f|^2}{9 + 6\text{Re}\{\chi_f\} + 4|\chi_f|^2}\right)|\vec{H}_{ext}|^2. \quad (12)$$

A finite element analysis program (COMSOL) was used to calculate $H_{ext}$ for given input current amplitude using a realistic, two-dimensional cross-section of the ferromicrofluidic channel and the electrodes underneath. The Reynolds' number associated with the motion of micron-scale beads and cells in a quiescent ferrofluid is very small. In this regime, inertial effects can be neglected and Stokes flow equations dominate hydrodynamics. Hence, the equilibrium between viscous drag and magnetic forces determine microparticle dynamics. Since Stokes flow equations are linear, all hydrodynamic coefficients involved can be combined into a resistance matrix:

$$\begin{bmatrix} F_{ave,x} \\ \tau_{ave,y} \end{bmatrix} = A\begin{bmatrix} v_x \\ \omega_y \end{bmatrix}, \text{ with} \quad (13)$$

$$A = \begin{pmatrix} 6\pi\eta R f_1(h, R) & 6\pi\eta R^2 f_2(h, R) \\ 8\pi\eta R^2 f_3(h, R) & 8\pi\eta R^3 f_4(h, R) \end{pmatrix}$$

(Happel J, Brenner H (1983) Low Reynolds Number Hydrodynamics with special applications to particulate media. (Martinus Nijhoff: Dordrecht)). Here, v is the linear velocity of the microparticle along the channel length, ω is its angular velocity, η is the ferrofluid viscosity, R is microsphere radius, and $f_i$ is a resistance factor that depends on particle radius and its distance (h) from the channel ceiling. Assuming h≪R, these resistance factors can be obtained from standard lubrication theory as $$f_1 \approx -8/15\ln(h/R) + 0.9588; f_2 \approx -2/15\ln(h/R) - 9.2526$$

$$f_3 \approx -1/10\ln(h/R) - 0.1895; f_4 \approx -2/5\ln(h/R) + 0.3817. \quad (14)$$

(Goldman et al., 1967, *Chem Engl Sci* 22:637-651). In general, it is possible to estimate h through Derjaguin, Landau, Verwey and Overbeek theory (DLVO theory) (Ise, 2007, *Proc Jpn Acad B Phys Biol Sci* 83:192-198) using the surface charge density on the microparticle and the channel surfaces, given the ionic conditions within the ferrofluid. Interestingly, the vertical force ($F_{ave,y}$) that pushes the microparticles up to the channel ceiling is on the order of nN's and they are expected to be close to touching the channel wall.

Equation (13) can be solved for v and ω through a simple matrix inversion, $$\begin{bmatrix} v_x \\ \omega_y \end{bmatrix} = A^{-1} \begin{bmatrix} F_{ave,x} \\ \tau_{ave,y} \end{bmatrix} \quad (15)$$

where $$A^{-1} = \frac{\begin{pmatrix} 8\pi\eta R^3 f_4(h,R) & -6\pi\eta R^2 f_2(h,R) \\ -8\pi\eta R^2 f_3(h,R) & 6\pi\eta R f_1(h,R) \end{pmatrix}}{48\pi^2 \eta^2 R^4 G}$$

Here $G=f_1 f_4 - f_2 f_3$ has been defined for notational convenience. Hence, particle linear velocities due to magnetic three and torque alone can be determined:

$$v_{force,x} = \frac{f_4}{6\pi\eta RG} F_{ave,x} \quad (16)$$

$$v_{torque,x} = -\frac{sf_2}{8\pi\eta R^2 G} \tau_{ave,y}. \quad (17)$$

Net particle, velocity is then given by $$v_x = v_{force,x} + v_{torque,x'} \quad (18)$$

Both magnetic force and torque scale with particle volume ($R^1$); from (16) and (17), it is clear that particle velocity due to magnetic force depends on $R^2$, whereas that due to torque scales with R. This observation indicates that torque effects on smaller particles is relatively more significant; and explains why smaller microparticles display smaller critical frequencies in their dynamics.

The preceding theoretical approach explains the experimental results very well (e.g., FIG. 4A) for a slip factor of 1 and h of about 1 nm, confirming the expectation that the microparticles are indeed pushed strongly towards the channel ceiling. The slip factor of 1 implies that the microspheres rotate under no-slip conditions.

Force on a Magnetic Dipole

In general the magnetic force on a magnetic dipole can be found using the Kelvin force expression, i.e., $$\vec{F} = \mu_0 \int_{V_P} (\vec{M} \cdot \nabla) \vec{H} dV \quad (19)$$

This expression h approximately equivalent to equation (1).

A key assumption is that the applied field is not too inhomogeneous and the particle radius (R) is small enough, such at $R|\nabla\vec{H}| \ll |\vec{H}|$ in any direction. Under this assumption, the magnetization of the ferrofluid immediately surrounding the microparticle can be taken as uniform. It is further approximated that any field value (but not its gradient) is constant within the interior extent of the microparticle.

With these simplifying assumptions in mind, vector identities can be used to rewrite the integrand of (1) as follows:

$$\nabla(\vec{M} \cdot \vec{B}) = \vec{M} \times (\nabla \times \vec{B}) + \vec{B} \times (\nabla \times \vec{M}) + (\vec{M} \cdot \nabla)\vec{B} + (\vec{B} \cdot \nabla)\vec{M}. \quad (20)$$

The first term on the right-hand-side (RHS) of (20) involves the curl of the magnetic flux density, which could be expanded as $$\vec{M} \times (\nabla \times \vec{B}) = \vec{M} \times (\nabla \times \vec{H}) + \vec{M} \times (\nabla \times \vec{M}) \quad (21)$$

The curl of the magnetic field is 0 everywhere within the integration volume of (1), since both the ferrofluid and the plastic microparticle are insulating and do not support electrical currents. Hence, the first term on the RHS of (21) vanishes. The curl of the magnetization is 0 inside the microparticle, but across its surface, the effective magnetization changes as a step. Therefore, surface contributions to the force density should, in general, be considered. However, since the magnetization of the ferrofluid immediately surrounding the microparticle is assumed to be constant, the second term of (21) also vanishes when integrated around a sphere (due to symmetry). The same logic could be applied to the $\vec{B} \times (\nabla \times \vec{M})$ term in (20): $(\nabla \times \vec{M})$ is 0 inside the microsphere and $\vec{B} \times (\nabla \times \vec{M})$ integrates to 0 around the sphere surface with the magnetic flux density and ferrofluid magnetization assumed constant in the immediate vicinity of the microsphere.

With the same reasoning, the $(\vec{B} \cdot \nabla)\vec{M}$ term to (20) will also be 0 inside the microsphere and integrate to 0 around it. The only term that involves the non-zero gradient of a field vector then is $$\vec{F} = \int_{V_P} (\vec{M} \cdot \nabla) \vec{B} dV. \quad (22)$$

The integral is valid over the volume of the microparticle, which is nonmagnetic. Hence, inside the nanoparticle, $\vec{B} = \mu_0 \vec{H}$ and (22) becomes the same as (19). In other words, under the assumptions outlined above, (1) and (19) are equivalent in the case of the setup presented herein.

The equation in (1) is preferably used as the force expression instead of that in (19), since the former leads to a force whose direction is determined by the gradient operator—requiring taking a single derivative along a given spatial direction to determine the force along that direction.

Also considered is what happens to surface gradients associated with the expression in (1). Once again, using the assumption that the ferrofluid magnetization and the magnetic flux density are constant inside and just around the microsphere surface (but not their derivatives), it can be determined that $$F_x = \int_{V_P} \frac{\partial}{\partial x}(\vec{M} \cdot \vec{B}) dV = \int_{V_P} \frac{\partial}{\partial x}(M_x B_x \cdot M_z B_z) dV \quad (23)$$

Here, the field and magnetization vectors are taken to be in the x-z plane due to the symmetry of the ferro-microfluid channel. In the previous section, the expression in (23) is evaluated only within the interior of the microparticle to calculate the x-directed force. Now, without any loss of generality, the microsphere center is taken as the origin. Both $\vec{M}$ and $\vec{B}$ are discontinuous at the particle-ferrofluid boundary, so their derivatives result in an impulse; when integrated across the microsphere surface, each contribution $M_{x,out}B_{x,out} - M_{z,in}B_{z,in}$ to the integral from a surface patch at $x=\sqrt{R^2-y^2-z^2}$ gets cancelled out by the negative of that contribution at the opposite patch at $x=-\sqrt{R^2-y^2-z^2}$. The resulting surface integral is 0. By spherical symmetry, the same is true for the terms in $F_2$. Hence, under the described assumptions, evaluating equation (1) within the interior of the microparticle yields the magnetic force on it.

System and Methods of Separation

Figure 9:
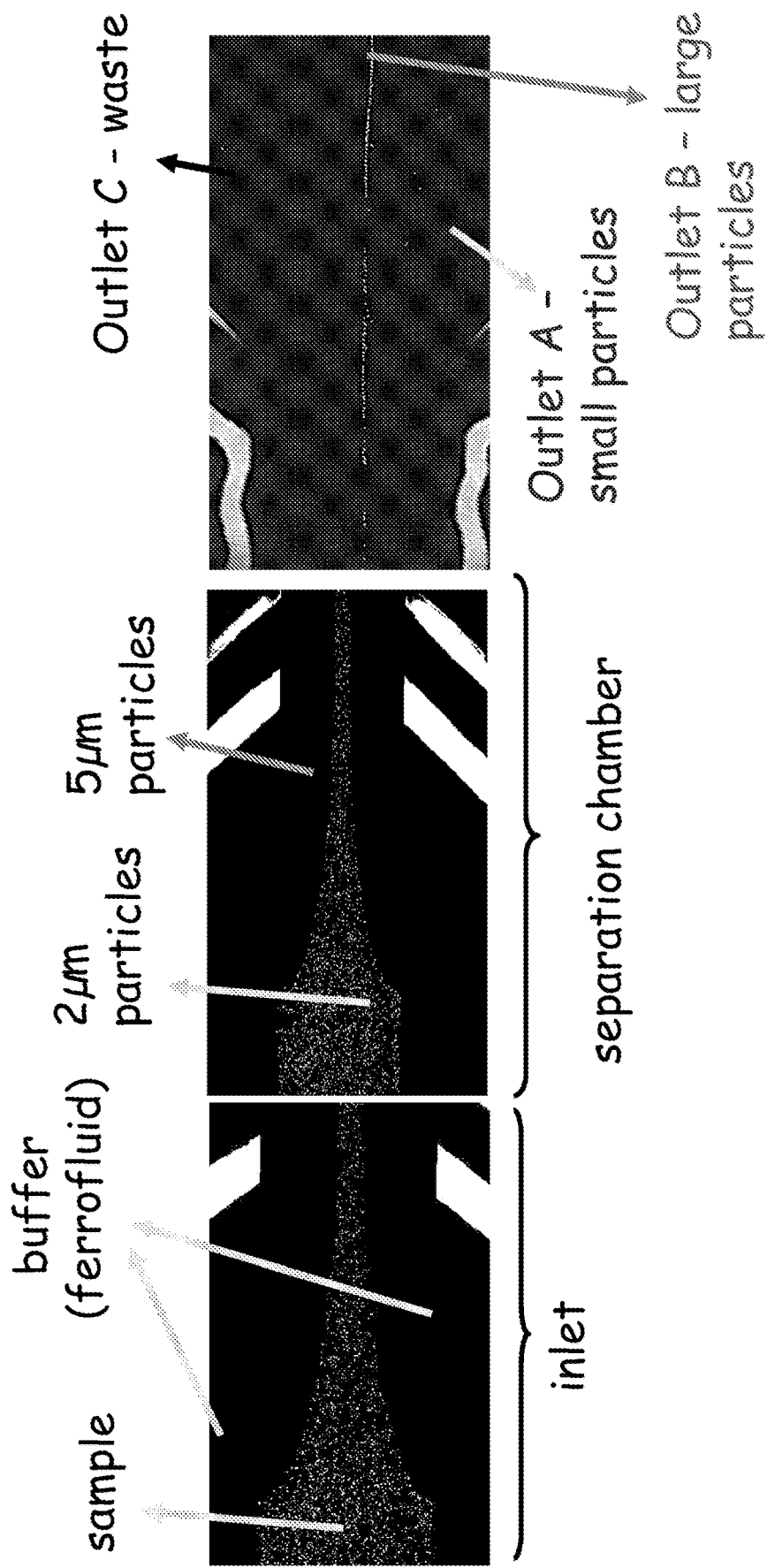
FIG. 9 depicts a continuous flow device allowing a sample suspended within the ferrofluid to enter the device inlet and pass through the separation chamber, and exit via multiple outlets designed for capturing particles of a particular size. The 2 µm particles flow to outlet A, the 5 µm particles flow to outlet B, and the remaining sample flows to a waste outlet C. The flow device depicted in FIG. 9 is thus suitable for sorting two or more particle types based on one or a combination of size, shape and elasticity.

The present invention also relates to a flow-based assay system incorporating the aforementioned biocompatible ferrofluids. In one embodiment, a much higher throughput can be achieved by conducting the bioferrofluidic separation while fluid flow continuously introduces fresh cells into the inlet of the channel. At the outlet, the incoming beads or cells are sorted into different output channels. From there, the cells can be collected for inspection or directed towards an external or internal (i.e., integrated) sensor. For example, the flow device allows a sample suspended within the ferrofluid to enter the device inlet and pass through the separation chamber, and exit via multiple outlets designed for capturing particles of a particular size. For example, as depicted in FIG. 9, 2 μm particles can flow to outlet A, 5 μm particles flow to outlet B, etc., and the remaining sample flows to a waste outlet C. In certain embodiments, flow is not needed to direct cells. Instead, magnetic excitation can be used to direct them. Further, the sensor may be directly integrated into a side pocket along the flow channel, for example.

Manipulation is not only dependent on cell size, but also on the shape and elasticity of the cells. For example, the variable size, shape and elasticity of bacteria and sickle cells allows them to be separated from healthy blood cells. According to an aspect of the present invention, particle separation can be dependent on size and frequency. In another embodiment, critical frequency, as described hereinthroughout, may also depend on the electrode gap. For example, larger microspheres can be trapped first in smaller gaps. By utilizing this phenomenon, sorting can be performed based on particle or target size. Further, the system may alternate between the manipulation excitation at the chosen frequency and another frequency that helps break possible nanoparticle chains that may form due to the magnetic excitation. According to an aspect of the present invention, "wiggly" electrodes can be used to prevent beads or cells from clustering into large chunks as they flow down the channel. The "wiggly" electrodes introduce disturbance forces and torques on the beads or cells to break clusters apart, allowing for larger individual beads or cells to line up like pearls on a necklace. By periodically breaking the nanoparticle chains, the ferrofluid physical properties are kept constant over time. Further, target cells can be concentrated, trapped, localized, or simply directed toward sensor surfaces efficiently, rapidly, and in a label-free fashion. For example, the method of separation can direct a cell or particle type based on size, shape or elasticity into an outlet, or by trapping a cell or particle type based on size, shape or elasticity via increasing or decreasing the spacing between electrodes.

Thus, the present invention includes a method for separating at least one cell type from a sample. The method includes the steps of suspending cells in a biocompatible ferrofluid to form a sample, passing the sample through a microfluidic channel that transverses a plurality of electrodes at about 90% such that the plurality of electrodes are substantially parallel to the length of the microfluidic channel, applying a current to the plurality of electrodes to create a magnetic field pattern along the length of the microfluidic channel, and sorting the cells into at least one output channel based on a variation of at least one of cell size, shape and elasticity. Separation can occur via concentrating, trapping, localizing, or simply directing toward sensor surfaces efficiently, rapidly, and in a label-free fashion.

The present invention also provides for a method for separating cells and/or particles based on side. This size-based separation can be demonstrated with about 50% efficiency, about 60% efficiency, about 70% efficiency, about 80% efficiency, about 905 efficiency, about 92% efficiency, about 94% efficiency, about 96% efficiency, about 97% efficiency, about 98% efficiency and about separation efficiency. Size revolution in the separation process can be less than shout 10 μm, less than about 9 μm, less than about 8 μm, less than about 7 μm, less than about 6 μm, less than about 5 μm, less than about 4 μm, less than about 3 μm, less than about 2 μm, less than about 1 μm, less than about 0.5 μm, less than about 0.1 μm, and less than about 10 nm. Such separation can be accomplished in less than about 2 m, less than about 1 m, less than about 45 s, less than about 30 sec, less than a hour 20 s, and less than about 10 s.

The present invention also provides for the continuous manipulation and shape-based separation of cells, such as live red blood cells from sickle cells and/or bacteria. These demonstrations highlight the ability of ferromicrofluidics to significantly reduce incubation limes and increase diagnostic sensitivity in cellular assays through rapid separation and delivery of target cells to sensor arrays.

The microfluidic system of the present invention has a number of unique advantages, in that it provides a laminar flow platform for use with tiny sample sizes. The system further provides fast diffusion and fast results, can be portable, and can be integrated with other existing sensors. For example, the present invention can be used for the sterilization of adult stem cells obtained from blood samples, for use in the context of wound healing and organ regeneration for soldiers and marines in combat. The present invention can also be used for the rapid detection (i.e., <1 min) of low-level bacterial contamination in donated blood. This can be particularly useful in battlefield trauma emergency situations. The present invention can also be utilized for "needle-in-haystack" applications that require the detection of ultra-low concentrations of cells in blood, such as searching for circulating tumor cells in blood.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Ferrofluid Preparation

A co-precipitation method was used to synthesize cobalt-ferrite nanoparticles that were eventually incorporated into a water-based ferrofluid with a 20% solid content (Khalafalla S E, Reimers G W (1973) U.S. Pat. No. 3,764,540). Cobalt-ferrite nanoparticles were precipitated out of a boiling solution of 1 M sodium hydroxide by adding a mixture of cobalt (II)-chloride hexahydrate and iron (III)-chloride. The magnetic precipitate was washed twice using DI water. 2 M nitric acid and a 0.35 M solution of iron (III)-nitrate were added to the precipitate (Massart, 1981, *IEEE Trans Magn* 17:1247-1248; Fischer et al., 2008, *IEEE Int Conf on Nano/Micro Eng and Molecular Syst* China, 907-910). This mixture was then stirred at 80° C. for 20 minutes. The nitric acid solution was then decanted while the precipitate was held in place with a magnet. Cobalt-ferrite particles within the precipitate were later dispersed in DI water, and the resulting ferrofluid was dialyzed for one week against a 40 mM sodium citrate and citric acid sedation at a pH level of 7.4. The solution was refreshed on a daily basis during dialysis. The resulting ferrofluid had a viscosity of 1.5 cP at 20° C.

TEM Sample Preparation

The TEM Images were using a Tecnai 12 electron microscope from Philips (120 keV). A copper/rhodium grid (from Electron Microscopy Sciences) was covered with a thin carbon film and dipped into a ferrofluid sample diluted with ethanol. After TEM images were obtained, particle sizes in the images were characterized using imageJ software (http://rsbweb.nih.gov/ij/). The distribution of magnetic nanoparticle core sizes, as obtained from the TEM images (around 200 particles counted), was fitted with a lognormal probability density function as $$F(D) = \frac{1}{\sqrt{2\pi} D\sigma} \exp\left(-\frac{(\ln D - \ln D_0)^2}{2\sigma^2}\right) \quad (24)$$

where D is the random variable depicting core diameter, while $D_0$ and $\sigma$ are the mean and standard deviation of ln(D), respectively.

AC Susceptibility Measurements

The frequency-dependent AC susceptibility of the ferrofluid can be obtained by measuring the changes in the mutual inductance of an electromagnetic coil pair, with and without the presence of a ferrofluid (Maiorov, 1979, *Magnetohydrodynamics* 15:135-139). In this regard, a pick-up coil (of 200 turns, with an average diameter of 9.76 mm) was centered within a solenoidal excitation coil (of 340 turns with an average diameter of 13.34 mm), and the mutual inductance of the two coils was characterized via an LCR meter for Agilent (E4980A). The ferrofluid sample was introduced within the two sets of coils in a 1 cc plastic syringe. The symmetry in the setup ensured parallel field lines at the location of the pick-up coil and enabled an analytical calculation of mutual inductance, and eventually, AC susceptiblity, from measured data.

The magnetization relaxation equation, assuming no fluid motion or convection (Rosensweig R E (1997) *Ferrohydrodynamics* (Dover: N.Y.)), is $$\frac{d\vec{M}}{dt} - \vec{\omega} \times \vec{M} = -\frac{1}{\tau}(\vec{M} - \chi_0 \vec{H}) \quad (25)$$

where $\omega$ is the local vorticity within the ferrofluid, $\chi_0$ is the DC susceptibility value of the ferrofluid, and $\tau$ is the magnetic relaxation time constant associated with the magnetic nanoparticles. The uniform magnetic field within the cylindrical setup leads to a symmetry that makes vorticity (and hence, the second term an (25)) negligible within the measurement volume. The magnetic relaxation time constant represents a combination of two physical relaxation processes. If the magnetic cores of the particles are small enough, their magnetic moment will simply rotate inside the nanoparticles (Néel relaxation) (Rosensweig R E (1997) *Ferrohydrodynamics* (Dover: N.Y.)) with a characteristic time constant given by $$\tau_N = \frac{1}{f_0} e^{(K_a V/k_B T)} \quad (26)$$

where $f_0$ is a precession frequency (typically in the range $10^8$-$10^{12}$ Hz), $K_a$ is a magnetic anistropy energy density, $V_{core}$ is the magnetic core volume of the nanoparticle, and $k_B T$ is the thermal energy. Particles with larger cores will have higher magnetic anisotropy energies, leading to fixed magnetic moments within the cores, and the particles themselves will rotate in solution to orient with the applied field (Brownian relaxation) with a characteristic time constant given by $$\tau_B = \frac{\pi D_{hyd}^3}{2k_B T} \eta \quad (27)$$

Here, $\eta$ the dynamic viscosity of the fluid, $k_B$ is the Boltzmann's constant, T is the absolute temperature (in Kelvins), and $D_{hyd}$ is the hydrodynamic diameter of the particle, including its surfactant layer. The faster of the two mechanisms dominates the relaxation process. Cobalt-ferrite possesses a high magnetic anisotropy energy density (between $1.8 \times 10^5$ and $3.0 \times 10^5$ J/m$^3$ for bulk material and up to $3.15 \times 10^6$ J/m$^3$ for nanoparticles (Tung et al., 2003, *J Appl Phys* 93:7486-7488)), and ferrofluids based on this material relax primarily by particle rotation (Brownian mechanism) above a critical nanoparticle size of about 5 nm in diameter. Since most of the nanoparticles observed in the TEM pictures were larger than this critical size, only the Brownian time constant was considered in interpreting our AC susceptibility measurements.

The sinusoidal steady-state solution to (25) in the absence of vorticity yields the concept of an effective susceptibility that describes the magnitude and phase relationship between ferrofluid magnetization and the applied field as a function of frequency f:

$$\chi(f) = \frac{\chi_0}{(1 + i2\pi f\tau)} = \frac{\chi_0}{(1 + (2\pi f\tau)^2)} - i\frac{2\pi f\tau \chi_0}{(1 + (2\pi f\tau)^2)} \quad (28)$$

(Debye P J W (1929) *Polar Molecules*. (Dover: N.Y)) Here, $\chi_0$ is the DC susceptibility value of the ferrofluid and $\tau$ is the Brownian relaxation time constant associated with the magnetic nanoparticles.

Ferrofluids consist of particles with a size distribution (typically lognormal), which leads to a distribution of the relaxation times as well. To take this into account, we describe the overall AC susceptibility as a linear combination of all susceptibility spectra that would result from the particle sizes present in the ferrofluid, weighed by the lognormal probability density function $F(D_{hyd})$ associated with a given particle size:

$$\chi(f) = \frac{1}{A}\int_0^\infty \frac{\chi_0}{(1+i(2\pi f \tau_B))}V_{core}^2 F(D_{hyd})dD_{hyd} \qquad (29)$$

The magnitude of the total magnetization within a nanoparticle is proportional to its core volume; so is its individual contribution to the susceptibility spectrum. Hence, the probability density function in (24) is scaled by $V_{core}^2$. The normalization factor A is given by $$A = \int_0^\infty F(D_{hyd})V_{core}^2 dD_{hyd} \qquad (30)$$

Figure 2A:
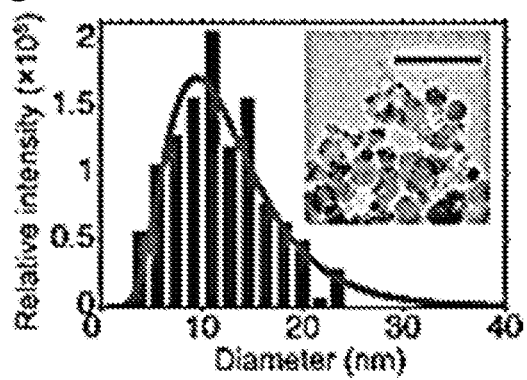
FIG. 2A is a graph depicting the distribution of cabaltferrite nanoparticle sizes within the ferrofluid, as obtained by TEM, Mean nanoparticle core diameter is 11.3±4.4 nm. (Scale bar: 50 nm.)
Figure 2B:
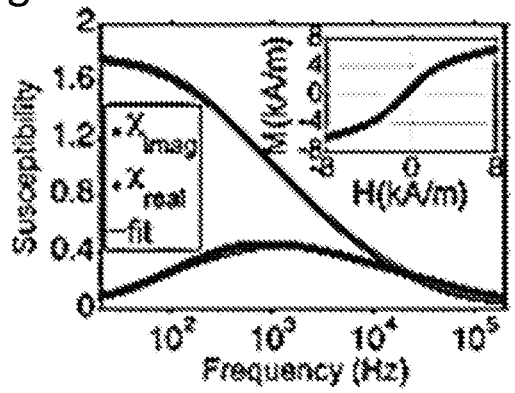
FIG. 2B is a graph depicting ac susceptibility and dc magnetization curve (Inset) of the ferrofluid. A fit to the ac susceptibility data assuming a log-normal size distribution indicates moderate particle aggregation with a mean hydrodynamic diameter of 72.5 nm.

The AC susceptibility data (FIG. 2B) can be fit with the sinusoidal steady-state solution to the magnetic relaxation equation assuming a log-normal distribution of hydrodynamic diameters (equations (27) through (30)). Simultaneously, the relative shape of the DC magnetization data (as depicted in FIG. 2B-inset) can be fit with the Langevin equation, once again assuming the same log-normal distribution of hydrodynamic diameters (and particle concentration as a free parameter). The simultaneous fits explain the experimental results very well, yielding an average hydrodynamic diameter of 72.5 nm. This value is much larger than the average core diameter of the nanoparticles as obtained with TEM. A reasonable explanation for this discrepancy is that, in equilibrium, the nanoparticles have formed moderate-sized aggregates that respond as single units to the magnetic fields that were applied during measurements. Dynamic light scattering experiments were also conducted on diluted samples of the same ferrofluid. Those results confirmed that the hydrodynamic diameters were much larger than the core diameters, supporting the explanation presented herein.

Typically, the surfactant concentration used is high enough to prevent continuous degradation in colloidal stability (at least over several months). Therefore, it is likely that the particle aggregates may have formed during one of the brief precipitation stages of the ferrofluid synthesis protocol, which often involves the use of a permanent magnet to speed the process. The surfactant is added later, and cannot break aggregates that have already formed.

Dynamic Light Scattering

The dynamic light scattering experiments were conducted using a ZetaPALS instrument from Brookhaven Instruments Group. For these measurements, the ferrofluid was diluted with DI water to avoid multiple scattering. The hydrodynamic particle diameter was found to be 64.9 nm.

Device Fabrication

The particle manipulation devise (FIG. 1A) used in the experiments presented herein consists of two parts: the microfluid channel and the underlying copper electrodes. The electrodes (30 μm high, 300 μm wide and 2 cm in length) were fabricated by wet etching the copper layer of a thermal-clad printed circuit board (on an insulated metal substrate) through a photoresist mask. A travelling magnetic field was generated in the channel by applying alternating currents in quadrature to a single layer of electrodes. The microfluidic channel (20 μm to 100 μm high, 1 mm to 3 mm wide and 2 cm to 3 cm long) was prepared from polydimethylsiloxane (PDMS) stamps through soft lithography and was bonded to an insulating layer of very thin PDMS covering the electrodes (Mao et al., 2006, *Nanotechnology* 17:34-47). The channel height was chosen to be well below the optimum for localized ferrohydrodynamic flow in order to minimize its potential effects on particle migration. In separate experiments with sub-micron tracer particles, no discernible hydrodynamic flow was observed. The insulated metal substrate allows efficient heat sinking, enabling AC currents up to 10 A at low voltages through the electrodes. Before introducing the ferrofluid/microsphere mixture into the microfluidic device, the channel was washed with a 1% triton-X solution for about 10 minutes in order to minimize particle attachment to the PDMS walls.

Microspheres

Different sizes (1.2 μm, 1.9 μm, 2.2 μm, 3.1 μm, 5.0 μm, 6.0 μm, 9.9 μm in diameter) of green fluorescent polystyrene microspheres were obtained from Duke Scientific (Fremont, Calif., USA). The coefficient of variation on the microsphere diameters was about 1%. These custom produced microspheres had a very low porosity and carried a minimal amount of charged groups on their surfaces. Microspheres were suspended in deionized (DI) wafer and kept at 4° C. until they were used in ferrofluid experiments.

PKH Cell Staining

To make the cells visible within the ferrofluid, blood cells were stained with green fluorescent membrane dye PKH67 (obtained from Sigma-Aldrich). This dye has an excitation peak at 490 nm and emission at 502 nm (Horan et al., 1989, *Nature* 340:167-168). Cell staining was performed by following the manufacturer's protocol with some modifications for our study.

General Preparation Protocol

Blood was drawn from donors prior to the experiments and kept at 4° C. prior to staining. Approximately 10 million cells were centrifuged and the plasma was subsequently removed. The cells were then suspended in 500 μl RPMI 1640 culture medium without serum (obtained from Invitrogen, Carlsbad, Calif., USA) and mixed well to remove any adherent and bound cells. The resulting suspension of cells was centrifuged again for 5 minutes at 1000 rpm.

The supernatant was carefully aspirated and the pellet was suspended in 500 μl Diluent C (supplied with the staining kit). Immediately after this, 4 micromolar PKH67 dye in Diluent C was prepared. Equal volumes of dye and cell solutions were mixed. The resulting cell suspension was incubated for 4 minutes, avoiding exposure to light. The staining reaction was stopped by adding an equal volume of fetal bovine serum (FBS) and the cell suspension was further incubated for 1 minute. The cells were then centrifuged for 5 minutes at 1200 rpm to remove the staining solution. They were washed three times in cell culture containing 10% FBS to remove any remaining dye in the solution. After washing was complete, the cells were suspended in culture medium. The brightness of labelled cells was tested with fluorescence microscopy. Before mixing with ferrofluid, the stained cells were washed with Dulbecco's phosphate buffered saline (PBS) buffer containing 10% FBS.

Cell Viability Test and Cell Counting

Citrate is an effective surfactant in ferrofluids, and it is mostly biocompatible in cell cultures as well. Therefore, citrate was utilized both to stabilize the ferrofluid and to provide an ionic medium for the cells to survive in. In this context, determining a novel and optimum citrate concentration was necessary, as too little or too much citrate would result in particle aggregation and precipitation within the ferrofluid. Further, cell survival within the ferrofluid depends on having enough ionic species to control the osmotic pressure on the cells to promote sustainability.

The highest citrate concentration within the ferrofluid that still resulted in a stable colloidal suspension of magnetic nanoparticles was determined to the about 40 mM. Higher citrate concentrations would begin to gradually destabilize the ferrofluid.

Figure 2C:
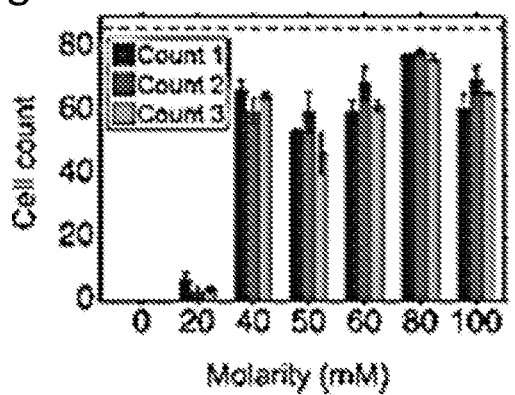
FIG. 2C is a chart depicting live cell count vs. citrate concentration. As shown herein, 40 mM citrate concentration (stabilized with citric acid to yield a pH of 7.4) is found to be optimum for cell viability and ferrofluid stability combined. The dashed line shows the cell count in the original blood sample. Count 3 corresponds to cells spending $\approx 1$ h in the citrate solution.

Cell viability was monitored using the Trypan Blue (obtained from Invitrogen) staining technique. Trypan Blue is a dye that selectively stains dead cells blue, allowing live and dead cells to be distinguished (The Sigma-Aldrich Handbook of Stains, Dyes & Indicators, Green, F. J., ed., Aldrich (Chemical Co. (Milwaukee, Wis.: 1990), 721-722). Following the manufacturer's protocol; 90 µl of 0.4% Trypan Blue Stain was added to 10 µl of the cell suspension with a concentration of $5 \times 10^5$ cells per 1 ml of culture medium. After incubation for 5 minutes at room temperature, a small sample from the mixture was placed onto a hemocytometer to count live cells. It was determined that the minimum concentration of citrate (stabilized with citric acid to result in a pH of 7.4) that first resulted in substantial cell survival over the course of several hours was 40 mM (FIG. 2C). At this ionic concentration, the cells were viable and the ferrofluid was stable. Hence, in all experiments involving cells suspended within our ferrofluid, a citrate concentration of 40 mM was used.

Example 1: Ferrofluid Properties and Device Characterization

Using highly concentrated ferrofluids with live cells has traditionally proven to be a challenge, because it requires a carefully engineered colloidal system. The ferrofluid parameters that are most relevant to sustaining live cells include pH, ionic strength, and nanoparticle-surfactant combination, together with their overall and relative concentrations. Finding the right nanoparticle-surfactant combination is crucial in this regard: the ferrofluid needs to be stable at a pH of 7.4, and colloidal stability has to be maintained up to an ionic strength that can sustain live cells. One also needs to pay special attention to the size distribution of the nanoparticles within the ferrofluid. If there exist nanoparticles only a few nanometers in diameter, they could pass through the cell membrane and cause direct cytotoxicity (Scherer et al., 2005, *Brazilian J Phys* 45:718-727). For this reason, the present invention includes a magnetic precipitation step in the synthesis of the biocompatible ferrofluids to specifically leave the smallest nanoparticles behind.

Traditional approaches to improving ferrofluid biocompatibility typically involve covering the magnetic nanoparticles permanently with a thick polymer layer, such as dextran (Bautista, et al., 2004, *Nanotechnology* 15:S154-S159), because the surfactant molecules reduce toxicity by impeding direct contact with the surface of the inorganic nanoparticles. However, such an approach leads to a significant reduction in the volume content of the magnetic nanoparticles within the ferrofluid, and a corresponding decline in its susceptibility. Higher ferrofluid susceptibility typically translates to faster particle manipulation, so the ferrofluid of the present invention has been optimized by using a short surfactant molecule.

In one embodiment, the ferrofluid of the present invention comprises cobaltferrite nanoparticles suspended in water and stabilized with citrate. Mean nanoparticle core diameter within the ferrofluid, as determined with transmission electron microscopy (TEM), was found to be about 11.3±4.4 nm (FIG. 2A). From simultaneous fits to ac susceptibility and dc magnetization data (FIG. 2B), the average hydrodynamic diameter was determined to be about 72.5 nm. The discrepancy between the average hydrodynamic diameter and the individual core sizes observed in TEM images points to a certain degree of particle aggregation within the colloidal suspension of the ferrofluid. This finding was also continued through dynamic light energy measurements, which yielded an average hydrodynamic diameter of about 64.9 nm on highly diluted samples ferrofluid. Nevertheless, compared with the µm-sized microspheres and cells, the magnetic nanoparticles were still small enough to approximate the ferrofluid as a continuous magnetic medium.

During synthesis, it was determined that the optimum ionic concentration within the ferrofluid to provide a good compromise between cell viability (as determined by the trypan blue test) and ferrofluid stability was about 40 mM (FIG. 2C). During the course of a given experiment, cells retained then viability. We observed that 75% of cells remained viable, even after being suspended in the ferrofluid for several hours, enabling extended tests involving live cell manipulation and separation.

Before the cell manipulation experiments, the ferromicrofluidic devices were characterized by using fluorescent polystyrene microspheres (Duke Scientific; monodisperse sets with diameters ranging from 1.2 to 9.9 µm). To understand the influence of excitation frequency and current amplitude on the behavior of nonmagnetic nanoparticles dispersed in ferrofluid, a series of experiments were performed using different sizes of microspheres at various excitation frequencies and current amplitudes. Microspheres of a given size were mixed with the ferrofluid in small quantities (up to $1.1 \times 10^6$ microspheres per mL for the smallest microparticle diameter) and subsequently added to the microfluidic channel. The channel inlet and outlet were clamped at both ends to prevent transient fluid motion. Microspheres near the roof of the microchannel were imaged from above with an upright fluorescent microscope (Zeiss Axiolmager A1) and a high-sensitivity video camera (Retiga 2000R) using StreamPix software. Image analysis was performed offline in MATLAB (MathWorks) via an optical flow algorithm. The program could automatically track the trajectory and determine the size of thousands of individual microspheres within the field of view in <1 min.

Figure 3A:
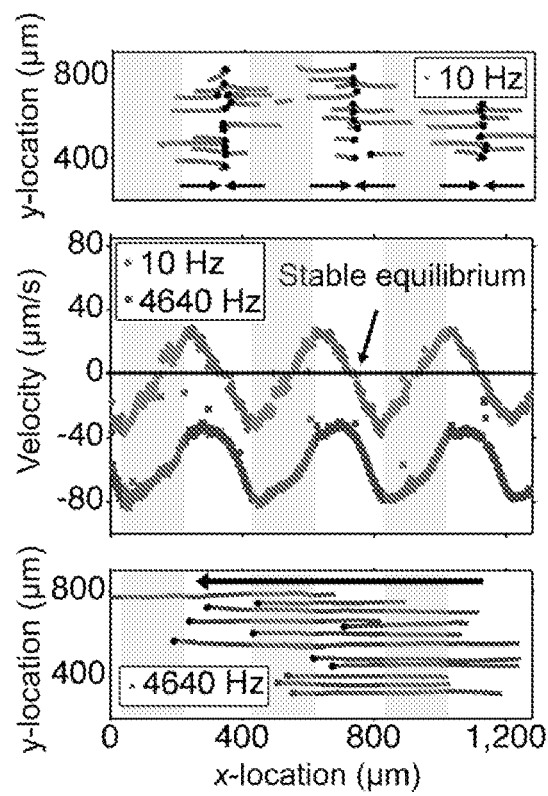
FIGS. 3A and 3B, is a demonstration of particle velocity as a function of input frequency and current amplitude.
Figure 3B:
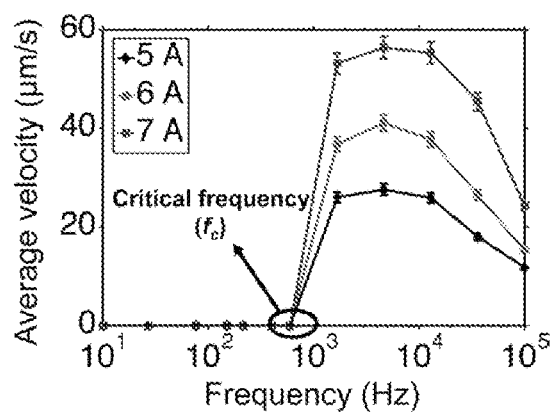

During these experiments, two types of particle dynamics were observed. At low frequencies, the microspheres localized between the electrodes, where repulsive forces caused by magnetic field gradients form local minima (FIG. 3A). Frequencies above a critical value, $f_c$, led to continuous translation of the microspheres along the length of the channel roof; this critical frequency depended only on particle size and electrode spacing, not on input current amplitude (FIG. 3B). The average velocity of microspheres of a given size depended on the excitation frequency, current amplitude, and their location with respect to the underlying electrodes.

Figure 4A:
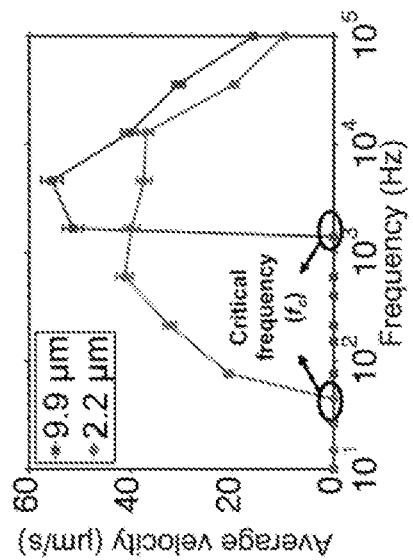
FIGS. 4A-4D, are illustrative of frequency-dependent particle separation.

In experiments with various microsphere diameters, a monotonic increase was found in critical frequency with increasing particle size (FIG. 4A), demonstrating the potential for size-based particle separation through excitation frequency control. This phenomenon may be explained through a simple hydrodynamic reasoning. Both magnetic force and torque scale with particle volume ($R^3$); the hydrodynamic drag that resists linear particle motion scales with R against force and $R^2$ against torque that rolls the particle. Hence, linear particle velocity caused by magnetic force alone depends on $R^2$, whereas that caused by torque scales with R. This observation indicates that torque effects on smaller particles are relatively more significant and explains why smaller microparticles can overcome the repulsion of magnetic force traps and propagate continuously within the channel at lower frequencies. The solid curve depicted in FIG. 4A represents simulation results for critical frequency and explains the data very well for an average microsphere-wall gap of ≈1 nm and no-slip conditions applied to the rotation of the microspheres.

Figure 4C:
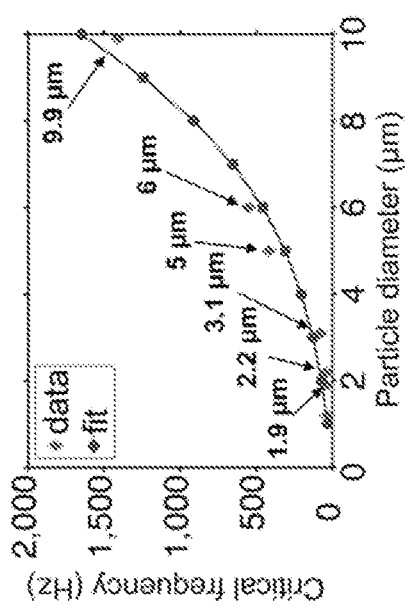
Figure 4B:
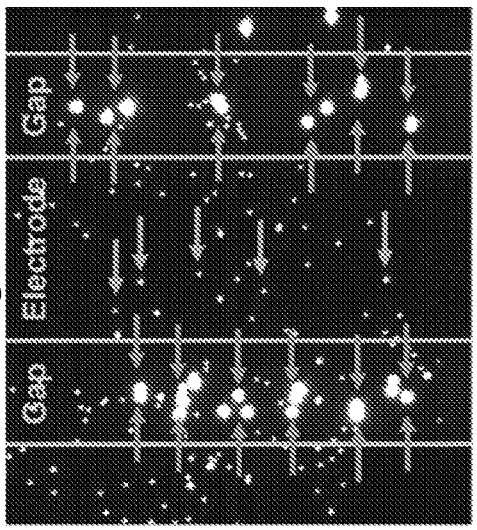
Figure 4D:
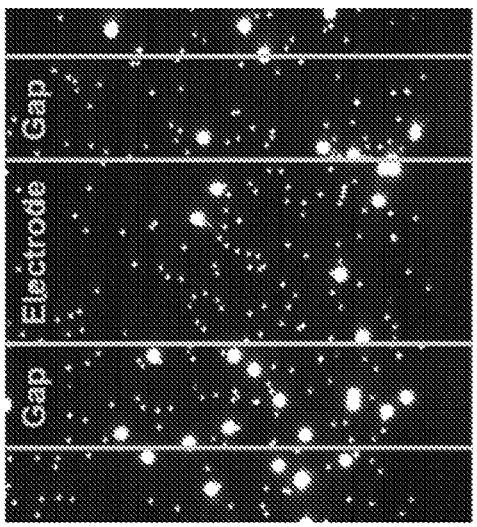

FIG. 4B shows the average velocity of 2,2- and 9,9-μm microspheres (mixed in an 8:1 ratio within the same ferrofluid) under excitation frequencies ranging from 10 Hz to 100 kHz. For a wide frequency range, the smaller particles translated continuously, whereas the larger particles were trapped between the electrodes. In this particular experiment and others, a mixture of particles/cells was eventually separated into two groups, e.g., those trapped vs. those cleared from channel. Assuming that the target particle-cells are those that are intended for trapping, the trapping efficiency can be defined as the ratio of the number of target moieties within the trapped group to their corresponding number in the initial mixture. Similarly, separation efficiency is defined as the ratio of the number of nontarget moieties within the cleared group to their corresponding number in the initial mixture. However, particle/cell purity is simply the ratio of the number of target cells within the trapped group to the total number of cells in that group. At an excitation frequency of 400 Hz, 96.5% of the 9.9 μm microspheres (167 of 173) were trapped within 10 s, whereas the 2,2-μm particles (1,285 of 1,294) continued to translate along the channel and were cleared out of the observation window (45 s) without being trapped (FIGS. 4C and 4D) with a 99.3% separation efficiency. The particle purity in the trapped group was 94.9% (167 targets of 176 total trapped particles). Most of the small microspheres that failed to clear the channel were stuck on the polydimethylsiloxane (PDMS) wall in random locations, instead of being trapped between the electrodes. With better channel preparation, the separation efficiency and particle purity can be even higher.

Figure 6A:
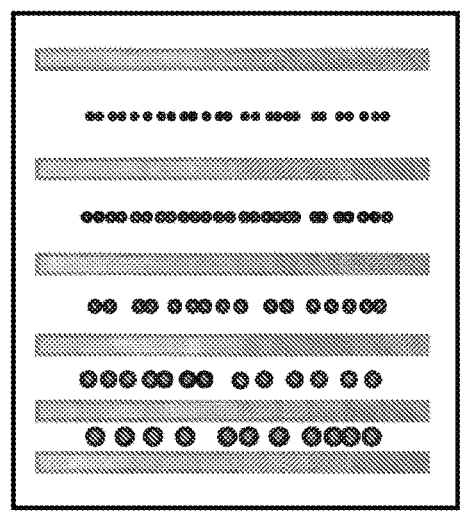
FIG. 6A depicts microparticle average speed, normalized by the square of the current amplitude (peak-to-peak) and to the maximum value at 5 A, depicted as a function of excitation frequency. Particle velocities are proportional to the square of current until about 7 A.
Figure 6B:
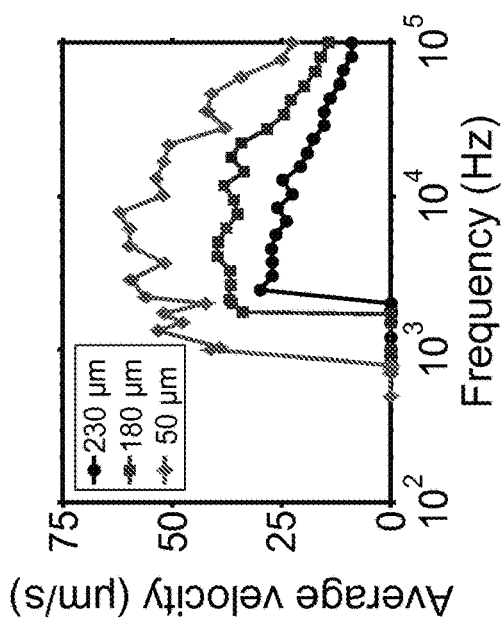
FIG. 6B depicts the average velocity vs. frequency at 6 A peak-to-peak for 9.9 µm microspheres travelling over electrodes with different spacings. A smaller spacing leads to higher particle velocity and a smaller critical frequency.
Figure 6C:
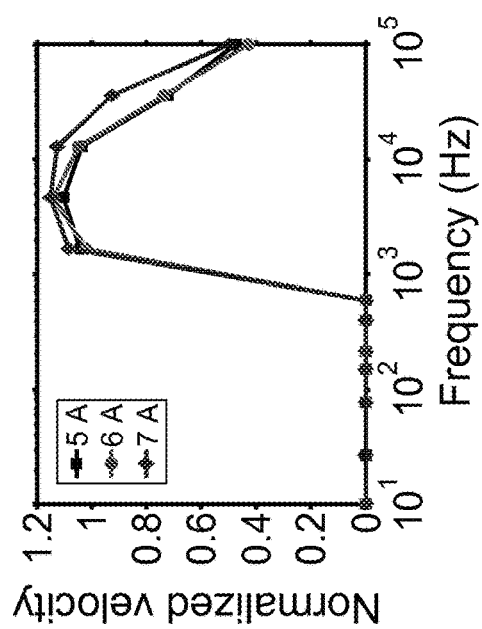
FIG. 6C depicts a conceptual sketch of a microparticle sorter based on the effect observed in 6C. At a given excitation frequency, smaller spacings trap larger particles, while letting smaller ones pass through. Eventually, even the smallest particles can be trapped in the larger gaps. Here, it is assumed that particles move from left to right, and the channel over the electrodes depicted is initially cell-free.

Particle motion was also determined to depend on electrode spacing, with a smaller spacing leading to faster microsphere travel and a reduction in critical frequency (FIG. 6B). This phenomenon may be used in a device featuring regions of electrodes with different gaps to use the same excitation frequency to separate particle mixtures with more than two distinct sizes. One could also create an electrode pattern with a gradually increasing gap to sort particles based on size (FIG. 6C). In this context, it was observed that small nonuniformities in actual electrode spacing (caused by fabrication) partly determined the resolution of separation, defined as the minimum size difference in particles that can still be separated with high efficiency (e.g., >90%). Given a range of particle sizes, this resolution of separation is directly related to the difference in the corresponding critical frequencies; under ideal conditions (i.e., perfectly controlled electrode gaps and a very dilute cell concentration), the resolution of separation could be arbitrarily small. However, critical frequencies tend to show slight local variations around each nonuniform electrode gap. As depicted in FIG. 4A, the ideal critical frequency depends nonlinearly on the particle radius; hence, a 1-μm difference in diameter between 9- and 10-μm microspheres is easier to resolve (with slight random variations in electrode spacing) than one between 1- and 2-μm particles. Ultimately the resolution of separation that was achieved in the experiments presented herein was ≈1 μm for particles 2 μm or larger.

Example 2: Effects of Current Amplitude on Microparticle Speed

In additional experiments, the dependence of microparticle manipulation speed as a function of input current amplitude was determined. According to the calculations outlined in herein, and assuming the ferrofluid remains magnetically linear, the particle speed scales with the square of the input current. As illustrated in FIG. 6A, this assumption begins to break above 7 A peak-to-peak input current amplitude.

Electrode spacing was also varied (with electrode width fixed at 210 μm) to determine its effect on particle manipulation. A smaller electrode spacing resulted in faster average particle speeds and lower critical frequencies (FIG. 6B). This observation could be explained by noting that electrodes spaced closer reduce the local magnetic field gradient that produces the magnetic force on the microparticles; closer electrodes also pack more energy into the fundamental of the travelling wave that produces the magnetic torque on these microparticles. A lower magnetic force and a higher torque result in faster microparticle rotation and overall travel speed; they also result in the critical frequency being lowered (Tung L D, et al. (2003) Magnetic properties of ultrafine cobalt ferrite particles. *J Appl Phys* 93:7486-7488). This observation supports the present invention for use as a microparticle sorting device in which the spacing between the electrodes could be gradually increased to trap increasingly smaller particles or cells (FIG. 6C).

Example 3: Separation of Live Cells

With the physical behavior of the ferromicrofluidic platform characterized, manipulation and separation experiments were conducted with live human red blood cells and bacteria to demonstrate the utility and practicality of the ferromicrofluidic devices of the present invention for biomedical applications. Red blood cells and *Escherichia coli* bacteria [K 12 strain (Blattner et al., 1997, *Science* 277: 1453-1474)] were stained with a green fluorescent marker and mixed before suspension in ferrofluid. The average velocity for cells and bacteria within the channel was measured with 6 A of peak-to-peak current amplitude for frequencies from 10 Hz to 100 kHz. The critical frequencies for cells and bacteria were found to be 215 and 77 Hz, respectively. These $f_c$ values are somewhat lower than those found for comparably sized polystyrene microspheres, likely due to a combination of compliant shapes and nonspherical geometries that lead to increased difficulty of rolling along the channel roof. Moreover, bacteria and cells, with their complex surface chemistries, interacted with the PDMS channel more strongly (resulting in more prevalent cellular attachment) than the bare microspheres, indicating potentially higher effective kinetic friction coefficients between the cells and the PDMS surface. FIG. 5A depicts the spatially averaged linear velocity of cells and bacteria along the channel for an excitation frequency of 200 Hz. The smaller *E. coli* move continuously along the channel (velocity points in FIG. 5A do not cross zero) and eventually left the observation window, whereas blood cells were localized between electrodes velocity points reach zero). Note that the larger variation observable in the red blood cell data FIG. 5A stems from a statistical fluctuation; there are only a few red blood cells that passed through a given x-location during the observation window, and their nonspherical shapes mean that each cell would be at a random angular orientation (and slightly different instantaneous velocity) as it rolled down the channel at that location. Bacteria, although varying in length and nonspherical, had enough numbers (several hundred through a given x-location) to result in good average statistics. In the end, ≈6,750 of the 7,050 *E. coli* bacteria initially present within the field of view of the sample were cleared (95.7% separation efficiency) within 45 s. Of the 1,018 red blood cells initially present, 954 were trapped, corresponding to a trapping efficiency of 93.7% and cell purity of 76.1%.

In a different experiment, healthy red blood cells were separated from those afflicted with sickle cell anemia by exploiting the shape and elasticity differences between them (FIG. 5B). A blood sample containing approximately a 4:1 ratio of healthy-to-sickle red blood cells was added to the ferrofluid and introduced into the microchannel. At 300 Hz, sickle cells were trapped, whereas the healthy blood cells were cleared continuously from the channel (fluctuations in each dataset depicted in FIG. 5B are statistical in nature). In a sample initially containing ≈501 healthy red blood cells and 145 sickle cells, 300 healthy cells were cleared, whereas 109 sickle cells were trapped. Assuming that the goal is to clear the sample from sickle cells, these numbers correspond to a separation efficiency of 75.2% (109 of 145 sickle cells were separated from healthy ones) and a healthy cell purity of 89.3% (300 healthy cells and 36 sickle cells were cleared).

These Examples demonstrate the use of ferromicrofluidics in significantly reducing incubation times and increasing diagnostic sensitivity in cellular assays through rapid separation and selective delivery of target cells to sensor arrays. While manipulation and separation of microparticles and live cells within microfluidic devices is also possible through established techniques (such as DEP and magnetic label-based methods), the ferromicrofluidic approach of the present invention offers numerous advantages over existing methods. For example, target cells can be concentrated, trapped, localized, or simply directed toward sensor surfaces efficiently, rapidly, and in a label-free fashion. The biocompatible ferrofluid of the present invention can sustain live blood cells for several hours without deterioration in physical properties, allowing extended examination of the target sample.

When combined with a simple photodiode, ferromicrofluidic separation of cells can provide a rapid, automated, and disposable blood assay that can count and estimate the concentration of any target cell type (such as bacteria or sickle cells) within 1 min, without the need for a microscope, pumps, or lengthy sample, preparation steps. The present invention can also be used to selectively concentrate rare cells, such as circulating tumor cells in blood samples, by exploding the differences in Young's modulus of the subject cell types (Lekka et al., 1999, *Eur Biophys J* 28:312-316). Applied in this manner, the present invention can increase detection sensitivity of existing cellular assays.

The present invention thus includes a cellular manipulation and separation platform using biocompatible ferrofluids within lowcost microfluidic devices. We have demonstrated highly efficient particle separation that is achievable in <1 min. As an example, bacteria can be separated from live blood cells, and sickle cells can be separated from healthy red blood cells. In the case of a flow-based device, separation can be achieved with particle manipulation perpendicular to the flow direction. By varying electrode geometry and input excitation frequency, the devices of the present invention can be tailored for different size ranges of particles and cells. Together with control of microchannel surface chemistry, the present invention can be integrated within lab-on-a-chip sensors and diagnostic systems to direct target cells toward active regions. In this manner, the present invention can significantly reduce incubation times and increase the practical detection sensitivities achieved in existing sensors and diagnostic platforms.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A device for separating a sample of particles suspended in a biocompatible ferrofluid, comprising:
   a microfluidic channel having a sample inlet, at least one output, and a length between the sample inlet and the at least one output, wherein a sample can be added to the sample inlet and flow along the length to the at least one outlet;
   a plurality of electrodes comprising a plurality of electrode layers, wherein the microfluidic channel length transverses at least a portion of the plurality of electrodes; and
   a power source for applying a current to the plurality of electrodes to create a magnetic field pattern along the length of the microfluidic channel.

2. The device of claim 1, wherein the spacing between electrodes is gradually increased.

3. The device of claim 1, wherein the spacing between electrodes is gradually decreased.

4. The device of claim 1, wherein the plurality of electrodes comprise at least one electrode layer.

5. The device of claim 1, wherein the plurality of electrode layers is in a substantially orthogonal pattern.

6. The device of claim 1, wherein the walls of the microfluidic channel length include a pocketed, a ridged, a grooved, a trenched or a sloped region.

7. The device of claim 1, wherein the microfluidic channel length transverses at least a portion of the plurality of electrodes at an angle between about 1-90 degrees.

8. The device of claim 1, wherein the particles are living cells.

9. A system for separating at least one target from a sample suspended in a biocompatible ferrofluid, comprising:
   a microfluidic channel having a sample inlet, at least one output, and a length between the sample inlet and the at least one output, wherein a sample can be added to the sample inlet and flow along the length to the at least one outlet;
   a plurality of electrodes, wherein the microfluidic channel length transverses at least a portion of the plurality of electrodes, and generating a magnetic field pattern along the length of the microfluidic channel when a current is applied to the electrodes; and
   at least one target in a sample suspended in a biocompatible ferrofluid;

wherein the at least one target is separated from the remaining sample as the at least one target passes along at least a portion of the microfluidic channel length, and wherein the at least one target is a cell or a particle.

10. The system of claim 9, wherein the sample comprises living cells.

11. The system of claim 10, wherein the biocompatible ferrofluid comprises a suitable amount of ionic species to control the osmotic pressure on the cells to promote cell sustainability.

12. The system of claim 11, wherein the biocompatible ferrofluid comprises a citrate concentration of between about 5-200 mM.

13. The system of claim 12, wherein the biocompatible ferrofluid comprises a citrate concentration of about 40 mM.

14. The system of claim 10, wherein the biocompatible ferrofluid has a pH of about 7.4.

15. The system of claim 9, wherein the at least one target is separated based on target size.

16. The system of claim 9, wherein the at least one target is separated based on target shape.

17. The system of claim 9, wherein the at least one target is separated based on target elasticity.

18. The system of claim 9, wherein the spacing between electrodes is gradually increased.

19. The system of claim 9, wherein the spacing between electrodes is gradually decreased.

20. The system of claim 9, wherein the target is separated by being directed to a selected outlet.

21. The system of claim 9, wherein the target is trapped based on the spacing of electrodes.

22. The system of claim 9, wherein the plurality of electrodes comprise at least one electrode layer.

23. The system of claim 9, wherein the plurality of electrodes comprise a plurality of electrode layers.

24. The system of claim 23, wherein the plurality of electrode layers is in a substantially orthogonal pattern.

25. The system of claim 9, wherein the plurality of electrodes comprise a pattern of concentric circles.

26. The system of claim 9, wherein the walls of the microfluidic channel length include a pocketed, a ridged, a grooved, a trenched or a sloped region.

27. The system of claim 9, wherein the microfluidic channel length transverses at least a portion of the plurality of electrodes at an angle between about 1-90 degrees.

28. A method for separating at least one cell type, comprising:
    suspending two or more cell types in a biocompatible ferrofluid to form a sample;
    passing the sample through a microfluidic channel that transverses a plurality of electrodes;
    applying a current to the plurality of electrodes to create a magnetic field pattern along the length of the microfluidic channel; and
    sorting the cells into at least one output channel based on a variation of at least one of cell size, shape and elasticity;
    wherein the cells are separated at an efficiency of at least about 90%.

29. The method of claim 28, wherein the biocompatible ferrofluid comprises a suitable amount of ionic species to control the osmotic pressure on the cells to promote cell sustainability.

30. The method of claim 29, wherein the biocompatible ferrofluid has a pH of about 7.4.

31. The method of claim 29, wherein the biocompatible ferrofluid comprises a citrate concentration of between about 5-200 mM.

32. The method of claim 31, wherein the biocompatible ferrofluid comprises a citrate concentration of about 40 mM.

33. The method of claim 28, wherein the separated cells are being directed to a selected outlet.

34. The method of claim 28, wherein the separated cells are being trapped based on the spacing of electrodes.

35. The method of claim 28, wherein the size resolution in separating is less than about 10 μm.

36. The method of claim 28, wherein the cells are separated in less than about 1 minute.

37. A system for separating at least one target from a sample suspended in a biocompatible ferrofluid, comprising:
    a microfluidic channel having a sample inlet, at least one output, and a length between the sample inlet and the at least one output, wherein a sample can be added to the sample inlet and flow along the length to the at least one outlet;
    a plurality of electrodes, wherein the microfluidic channel length transverses at least a portion of the plurality of electrodes, and generating a magnetic field pattern along the length of the microfluidic channel when a current is applied to the electrodes; and
    at least one target in a sample suspended in a biocompatible ferrofluid;
    wherein the at least one target is separated from the remaining sample as the at least one target passes along at least a portion of the microfluidic channel length, and
    wherein the microfluidic channel length transverses at least a portion of the plurality of electrodes at an angle between about 1-90 degrees.

* * * * *